US010366463B2

(12) United States Patent
Fialkov

(10) Patent No.: US 10,366,463 B2
(45) Date of Patent: *Jul. 30, 2019

(54) METHOD AND SYSTEM FOR INFORMED CONSENT

(71) Applicant: Rational Surgical Solutions, LLC, Des Moines, IA (US)

(72) Inventor: Jonathan Fialkov, Des Moines, IA (US)

(73) Assignee: Rational Surgical Solutions, LLC, Des Moines, IA (US)

( * ) Notice: Subject to any disclaimer, the term of this patent is extended or adjusted under 35 U.S.C. 154(b) by 628 days.

This patent is subject to a terminal disclaimer.

(21) Appl. No.: 14/622,978

(22) Filed: Feb. 16, 2015

(65) Prior Publication Data

US 2016/0110832 A1 Apr. 21, 2016

Related U.S. Application Data

(60) Provisional application No. 62/065,850, filed on Oct. 20, 2014.

(51) Int. Cl.
*G16H 10/60* (2018.01)
*G16H 80/00* (2018.01)
*G06Q 10/00* (2012.01)
*G06Q 50/22* (2018.01)

(52) U.S. Cl.
CPC ............ *G06Q 50/22* (2013.01); *G06Q 10/00* (2013.01); *G16H 10/60* (2018.01); *G16H 80/00* (2018.01)

(58) Field of Classification Search
USPC ....................................................... 705/2, 3
See application file for complete search history.

(56) References Cited

U.S. PATENT DOCUMENTS

| | | | |
|---|---|---|---|
| 6,171,112 B1 * | 1/2001 | Clark | G06Q 50/22 434/322 |
| 8,190,446 B2 | 5/2012 | Sobel | |
| 8,233,672 B2 * | 7/2012 | Matos | G06K 9/00 340/5.53 |
| 8,655,796 B2 | 2/2014 | Udani | |
| 8,909,811 B2 | 12/2014 | Margolis et al. | |

(Continued)

OTHER PUBLICATIONS

Hood CA, Hope T, Dove P. Videos, photographs, and patient consent.BMJ: British Medical Journal. 1998;316(7136):1009-1011. (Year: 1998).*

(Continued)

*Primary Examiner* — Rachel L. Porter
(74) *Attorney, Agent, or Firm* — McKee, Voorhees & Sease, PLC

(57) ABSTRACT

A method for documenting informed consent includes obtaining a video recording of a patient indicative of informed consent, communicating the video recording across a network for data storage, and storing the video recording in a computer readable data storage medium. The video may include additional portions of a patient encounter. A software application for executing on a computing device may provide a user interface for obtaining video evidencing informed consent for the procedure, administering a quiz to the individual, presenting a document for signature to the individual, receiving a signature for the document from the individual.

6 Claims, 29 Drawing Sheets

(56) References Cited

U.S. PATENT DOCUMENTS

| | | | |
|---|---|---|---|
| 2003/0139942 A1* | 7/2003 | Rakshit et al. | G06F 19/324 705/2 |
| 2006/0282292 A1* | 12/2006 | Brink | G06F 19/363 705/3 |
| 2010/0092937 A1* | 4/2010 | Jackson | G09B 19/0076 434/262 |
| 2012/0035949 A1 | 2/2012 | Brink et al. | |
| 2012/0127157 A1* | 5/2012 | Adler | A61B 5/0022 345/419 |
| 2012/0310670 A1* | 12/2012 | Pruitt | G06Q 10/10 705/3 |
| 2013/0019149 A1 | 1/2013 | Spencer et al. | |
| 2013/0149683 A1* | 6/2013 | Steerman | G09B 19/00 434/236 |
| 2014/0141397 A1* | 5/2014 | Dunn | G09B 5/02 434/262 |
| 2015/0046174 A1* | 2/2015 | Mainwaring | G06F 19/3456 705/2 |

OTHER PUBLICATIONS

Kulkarni, Niranjan et al., "Audio-video recording of informed consent process: Boon or bane" Perspectives in Clinical Research, Jan.-Mar. 2014, vol. 5, Issue 1, pp. (Year: 2014).*

"The Patient Education Materials Assessment Tool (PEMAT) and User's Guide", http://ahrq.gov/sites/default/files/publications/files/pemat-av.pdf, available online Aug. 19, 2015.

* cited by examiner

Consent for Surgery or Procedure

- Please read the form.
- Ask about any part you do not understand.
- Be sure you have your questions answered before you sign this form.
- When you sign it, you are giving us permission to do this surgery or procedure.

I, Anthony Wallace _____ (patient's name) agree for Dr. _____
along with any assistants the doctor may choose, to do this surgery or procedure on me at: _____
Name of licensed facility
Radical Retropubic Prostatectomy with Pelvic Lymph Node Dissection
_____

Name of surgery or procedure in medical words--including left, right, or level
(Doctor or health care worker fills this out)

Name of surgery or name of procedure in my own words
(What the patient or family says back to the doctor or health care worker--quote patient or family)

1. I understand that my doctor may find other medical conditions he/she did not expect during my surgery or procedure. I agree that my doctor may do any extra treatments or procedures he/she thinks are needed for medical reasons during my surgery or procedure.
2. I understand I may be given medicine to put me to sleep, make parts of my body numb, or help control pain. People with special training will give this medicine. These people may be an anesthesiologist, a nurse anesthetist (CRNA), a nurse, or the doctor doing my surgery or procedure.
3. I understand the doctor may remove tissue or body parts during this surgery or procedure. If it is not used for lab studies or teaching, it will be disposed of, as the law requires.
4. I understand I may be given a substance during an x-ray, if needed, so the tissue in my body can be better seen on the exam.
5. I understand pictures or video of my surgery or procedure bay be taken, if my doctor thinks it is needed for medical reasons.
6. I understand someone may watch or help with my surgery or procedure for medical teaching. These people are usually medical or nursing students. A technical advisor may watch if my doctor thinks one is needed.
7. I understand that if my doctor thinks I need blood for medical reasons, it will be given.

*FIG. 21*

METHOD AND SYSTEM FOR INFORMED CONSENT

CROSS REFERENCE TO RELATED APPLICATIONS

This application claims priority under 35 U.S.C. § 119 to provisional applications U.S. Ser. No. 62/065,850 filed Oct. 20, 2014, herein incorporated by reference in its entirety.

FIELD OF THE INVENTION

The present invention relates to technology for obtaining and retaining records of informed consent.

BACKGROUND OF THE ART

Although the present invention has uses in various areas, the background of the invention is discussed with respect to particular problems in the medical profession. The invention is not, however, necessarily limited to these particular medical applications.

In medicine, informed consent is important. Generally informed consent involves health care providers providing complete information about the nature of a medical procedure or other event. This information can include information about possible complications, who is performing the procedure, and other relevant information which may vary depending on the circumstances. The patient needs to understand what is being conveyed and be competent to make a decision in view of the information provided by the health care provider. This process is consistent with medical ethics.

Informed consent is generally obtained by having the patient sign a document indicating that they have provided their informed consent after they have had a discussion with their health care provider and/or reviewed appropriate written materials. This step is helpful for legal reasons as the patient contractually agrees that they have given their informed consent. Failure to obtain consent can result in claims of battery, negligence, or other legal claims against a health care provider regardless of whether medical procedures were performed competently. Despite written consent, problems remain.

For example, patients may fail to recall conversations with the health care provider and informed consent documents may not always capture all information discussed between patients and health care providers or establish that patients had the opportunity to have all of their questions and concerns addressed. What is needed is a technological solution which improves the informed consent process.

SUMMARY

Therefore, it is a primary object, feature, or advantage of the present invention to improve over the art.

It is a further object, feature, or advantage of the present invention to obtain informed consent from patients in a manner consistent with the highest order of medical ethics.

It is a still further object, feature, or advantage of the present invention to improve the communications between health care provider and patient in situations where informed consent is needed.

Another object, feature, or advantage of the present invention is to improve upon the documentation of informed consent.

Yet another object, feature, or advantage of the present invention is to eliminate or defend against frivolous claims for failure to obtain informed consent.

Another object, feature, or advantage is to provide a method of obtaining informed consent which can be used in different industries.

Yet another object, feature, or advantage is to provide a software application with the ornamental design as shown.

One or more of these and/or other objects, features, or advantages of the present invention will become apparent from the specification and claims that follow. No single embodiment need exhibit each and every object, feature, or advantage and different embodiments may have different objects, features, or advantages.

According to one aspect, a method for documenting informed consent is provided. The method includes obtaining a video recording of a patient indicative of informed consent, communicating the video recording across a network for data storage, and storing the video recording in a computer readable data storage medium. The method may further include positioning at least one video camera in a room associated with a health care provider in which the patient provides the informed consent. The method may further include retrieving the video recording of the patient indicative of informed consent over the network and from the computer readable storage medium. The method may further include providing a user interface to the health care provider for accessing the video recording. The method may further include combining data from a health care information system with the video recording. The video recording may further include at least a portion of a patient encounter. The method may further include making the video recording available to the patient through a portal. The method may further include making the video available to the patient by placing the video on a USB drive.

According to another aspect, a method for obtaining and documenting informed consent is provided. The method includes providing a software application to a computing device for executing on the computing device, receiving a selection of an individual into the software application executing on the computing device. The method may further include receiving a selection of a procedure for which informed consent is desired into the software application executing on the computing device, capturing video evidencing informed consent for the procedure using the software application executing on the computing device and making available a quiz for the individual using the software application executing on the computing device, the quiz including a plurality of questions about the procedure for assessing informed consent. The method may further include documenting administration of the quiz to the individual using the software application executing on the computing device, presenting a document for signature to the individual using the software application executing on the computing device, the documenting indicative of informed consent for the procedure. The method may further include receiving a signature on the document from the individual using the software application executing on the computing device, and sending to a server from the computing device the video, the document with the signature, and storing the video in a non-transitory computer readable data storage medium associated with the server to thereby provide for documenting the informed consent of the individual for the procedure.

The capturing video is performing may be performed using a camera integrated into the computing device. The method may further include receiving a selection of an option to bypass the quiz and documenting a reason for bypassing the quiz by sending the reason to the server. The procedure may be a medical procedure and the individual may be a patient. The video may include video of the patient acknowledging that they are providing informed consent. The method may further include making the video available to the individual through a portal associated with the server. The method also may further include making the video available to a service provider of the individual through a portal associated with the server. The video may include video of the individual and a service provider interacting with the individual. The method may further include receiving through the software application setting information identifying a plurality of procedures and one more procedure types. The method may further include receiving through the software application the document associated with the procedure. The method may further include receiving through the software application the plurality of questions about the procedure. The software application may be a mobile app and the computing device may be a mobile computing device.

According to another aspect, a method for obtaining and documenting informed consent for a procedure from an individual is provided. The method includes providing a software application to a computing device for executing on the computing device wherein the software application provides a user interface for obtaining video evidencing informed consent for the procedure, administering a quiz to the individual, presenting a document for signature to the individual, receiving a signature for the document from the individual. The method further includes receiving a selection of a procedure for which informed consent is desired into the software application executing on the computing device, capturing the video evidencing informed consent for the procedure using the software application executing on the computing device, and presenting the document for signature to the individual using the software application executing on the computing device, the documenting indicative of informed consent for the procedure. The method may further include receiving the signature on the document from the individual using the software application executing on the computing device and sending to a server from the computing device the video, the document with the signature, and storing the video in a non-transitory computer readable data storage medium associated with the server to thereby provide for documenting the informed consent of the individual for the procedure. The method may further include administering the quiz for the individual using the software application executing on the computing device, the quiz including a plurality of questions about the procedure for assessing informed consent. The method may further include documenting administration of the quiz to the individual using the software application executing on the computing device and sending a record of the administration of the quiz to the server from the computing device.

According to another aspect, a system is provided for obtaining and documenting informed consent. The system may include a software application for executing on a computing device wherein the software application provides a user interface for obtaining video evidencing informed consent for the procedure, administering a quiz to the individual, presenting a document for signature to the individual, receiving a signature for the document from the individual.

BRIEF DESCRIPTION OF THE DRAWINGS

FIG. 21 is a screen display showing a mobile app with a consent for surgery or procedure document.

DETAILED DESCRIPTION

The present invention provides for a comprehensive system and related methods for obtaining informed consent including video records of informed consent. Primarily, the invention will be described with respect to a software application suitable for use on a mobile computing device which may be referred to as a "mobile app." It is to be understood, however, that the software application described may execute on any number of different types of computing devices including desktop computers, notebook computers, tablets, wearable computers, phones, or other types of computing devices. The computing device may use any number of different types of operating systems including iOS, Android, Blackberry, Windows, or other operating systems. The software may be written in any number of different types of languages using any number of different types of platforms or tools. As shown herein the mobile app is executing on an Apple iPAD with an iOS operating system which provides a touch screen interface. The Apple iPAD also includes multiple video cameras.

Figure 1A:
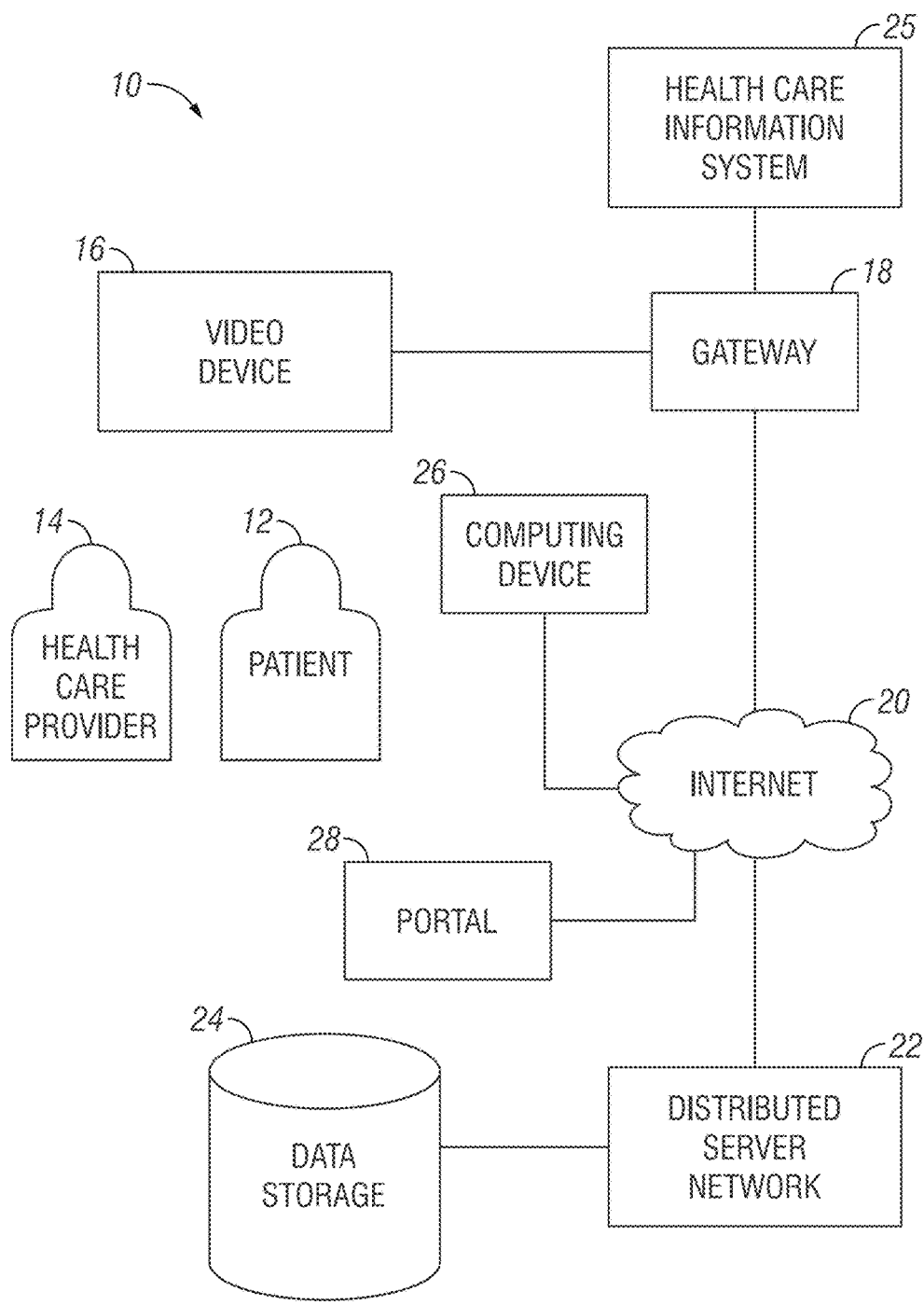
FIG. 1A is a diagram illustrating one example of a system for obtaining informed consent using video.

FIG. 1A illustrates a system 10. A patient 12 and health care provider 14 are shown. A video device 16 is shown which may be used to acquire audio and video of the patient 12 and/or interactions between the patient 12 and the health care provider 14. The video device 12 may include one or more cameras or other imaging devices located in a patient examination room, office, or other location in a physician's office or other health care facility.

One or more video devices 16 may be operatively connected to a gateway 18. The gateway 18 may be operatively connected to the internet 20. The internet may be operatively connected to or include a distributed server network 22. The distributed server network 22 may be operatively connected to data storage 24.

In addition, it is also contemplated that one or more health care information systems 25 associated with the practice of the health care provider may also be operatively connected to the gateway 18. It is contemplated that information from the health care information system 25 may be combined with the video either automatically or manually to identify the video such as with a unique patient identifier, type of procedure for which informed consent is given, or other information. In addition, stored videos may be made available to the health care information system 25.

In operation, a health care provider 14 may discuss with a patient 12 an upcoming medical procedure, the attendant risks, who will be performing the procedure, possible complications, and other relevant information. The patient 12 may ask questions that they have about the procedure, confirm that they have read appropriate literature and verify that they are giving consent. The patient may then sign a written document confirming that they have been provided informed consent or electronically sign a document confirming that they are providing informed consent. During this, or any other interaction, the video device 16 may record relevant audio and video. Thus, a record of all or a part of the interaction may be recorded. For example, the portion of the interaction where the client signs the informed consent may be recorded. The patient may be asked to read a statement confirming their consent on the video. The video may then be communicated through the gateway 18 and the internet 20, over a distributed server network 22 and to data storage 24. The video may then be made available to a computing device 26 for playback by the health care provider 14. In some embodiments, the video may also be made available to the patient 12. The video may be made available to the patient 12 through a web site portal, mobile app, or other portal 28. Alternatively, the video may be available to the patient by storing the video for the patient on a computer readable storage medium such as a USB drive. The communication and storage of the video are performed securely in a manner consistent with all applicable health privacy laws and regulations.

As described, the method and system provides for a number of different advantages. First, there is a more complete record of the informed consent. Patients are more apt to remember the interaction leading up to the informed consent when acknowledgement of the informed consent is made for video archive purposes. Patients are also more likely to appreciate the importance of the informed consent when (in their view) the process involves more than merely a form to sign but a video recorded confirmation of their consent. In addition, the video would provide additional evidence in legal proceedings which would be highly relevant to the legal determination of whether informed consent was provided or not.

In situations where all or a portion of the interaction between the health care provider and patient is recorded an additional record of the complete interaction between health care provider and patient is made. Another potential benefit is that this may potentially be shared with the patient for their records in case they want to review information conveyed to them before their procedure. This information may be shared through a web site portal, through a mobile app, or may be stored on a computer readable storage medium such as a USB drive.

Where all or a portion of the interaction between the health care provider and the patient is recorded this may also be advantageous in showing the patient that the health care provider is being very transparent in their communications and that informed consent is being provided in an appropriate manner.

Figure 1B:
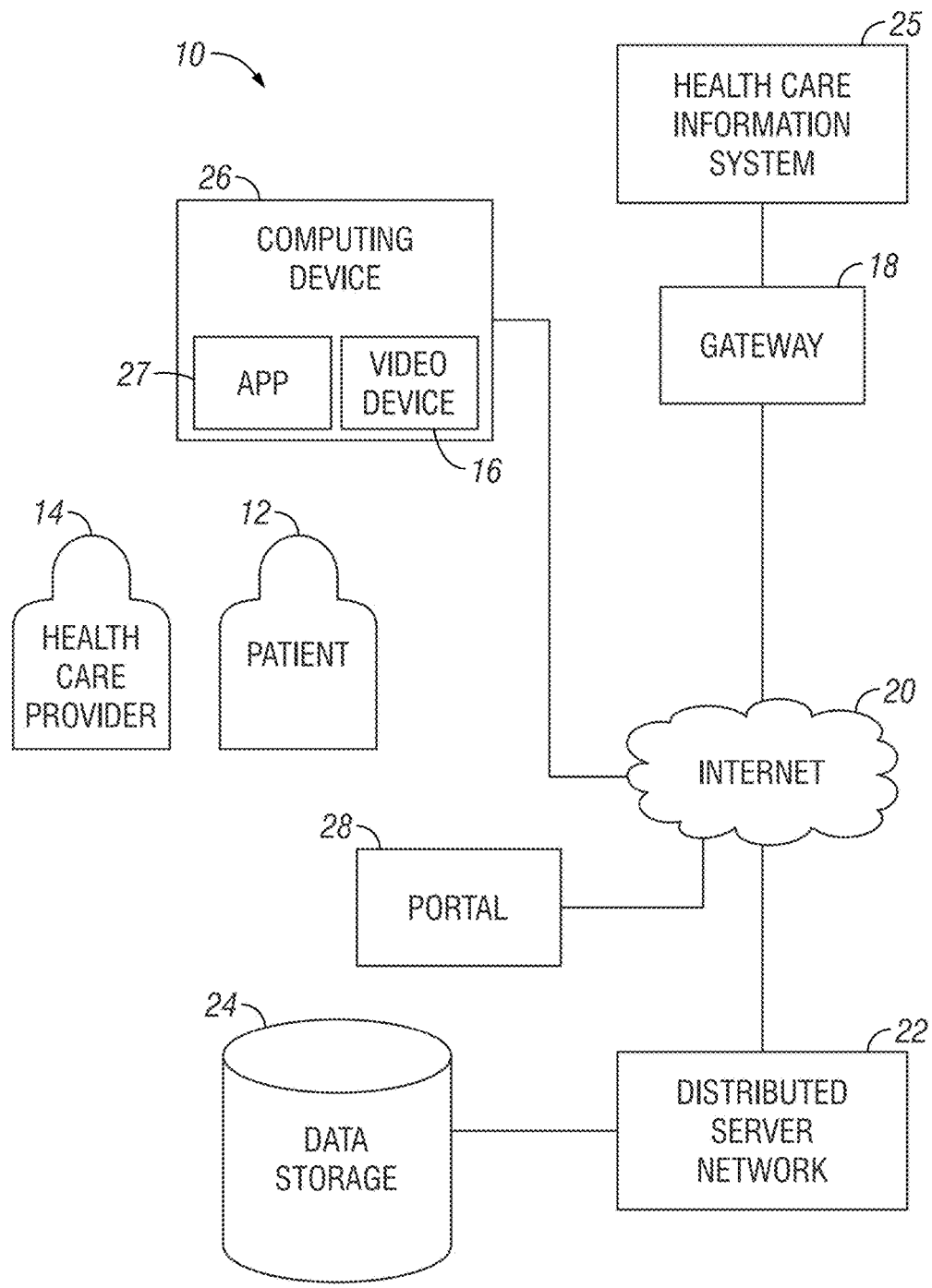
FIG. 1B is another diagram illustrating another example of a system for obtaining informed consent using video.

As previously discussed, in one embodiment the video camera may be mounted or otherwise positioned in a patient examination room or other room. Alternatively, a video camera associated with a mobile device or other computing device such as a tablet computer may be used to record the informed consent. Where used, the video may be wirelessly communicated to the gateway 18 shown in FIG. 1A.

Where a mobile device is used, any documents pertaining to informed consent may be signed in addition to video being recorded. FIG. 1B illustrates an embodiment with a computing device 26 which includes a non-transitory computer readable memory for storing an app 27. One or more cameras or other imaging devices 16 may be a part of the computing device 26. The computing device 26 may, for example, be a mobile device such as a tablet computer.

Although a health care provider 14 and a patient 12 are shown it is to be understood that the health care provider is one example of a service provider and the patient may be a customer or client. In addition, the health care information system 25 may be another type of information system associated with a different type of business.

Figure 2:
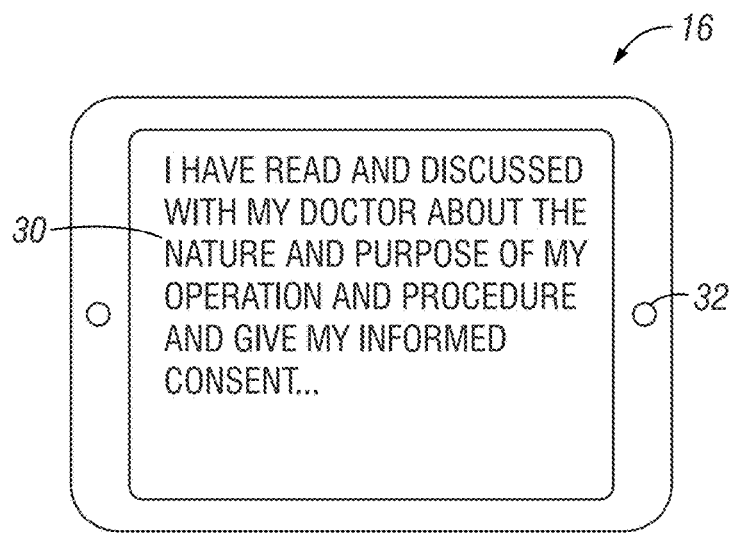
FIG. 2 is a diagram.

FIG. 2 illustrates an example of a mobile device 16 with a display 30 and a camera 32. In one embodiment, the patient may be asked to read a statement re-affirming their informed consent while on camera.

Figure 3:
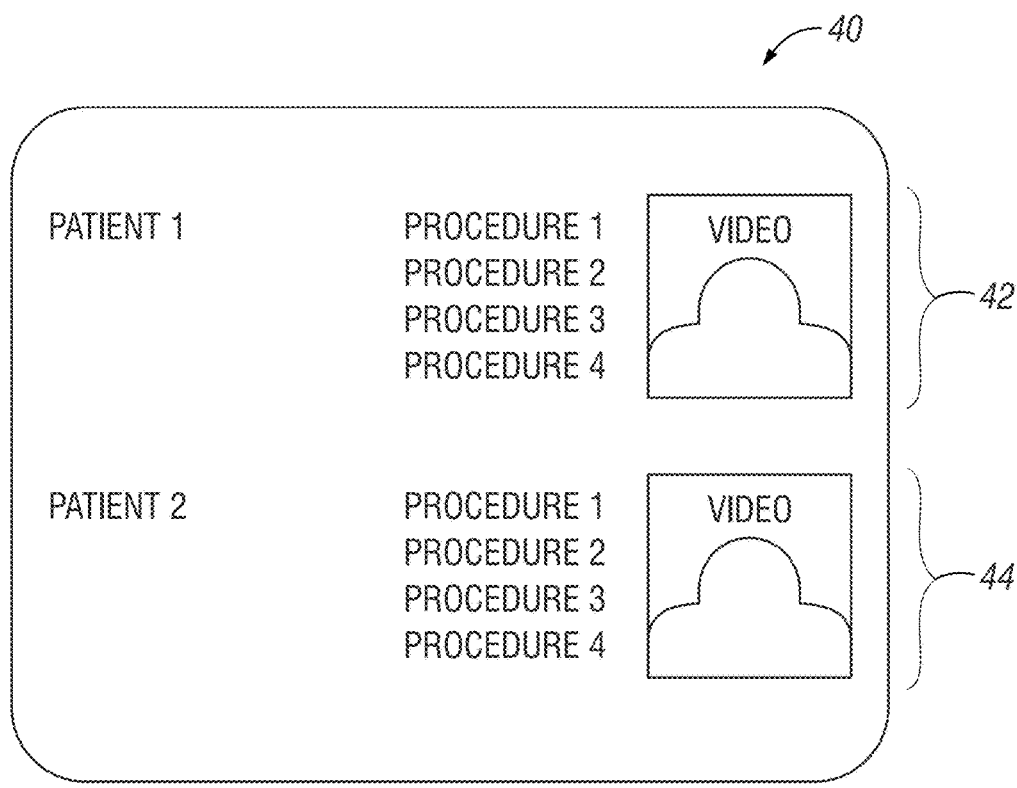
FIG. 3 is a screen display of a user interface for a health care provider to review informed consent videos.

Once the informed consent videos are stored they may be accessed as needed. FIG. 3 is an example of a screen display 40 illustrating that for each patient there may be one or more examples of informed consent they have given on different occasions and corresponding video is also made available. Thus as shown, for a first patient there are multiple procedures and videos 42 listed and also for a second patient there are multiple procedures and videos 44 listed. Thus, the health care provider has a record of the informed consent.

Figure 4:
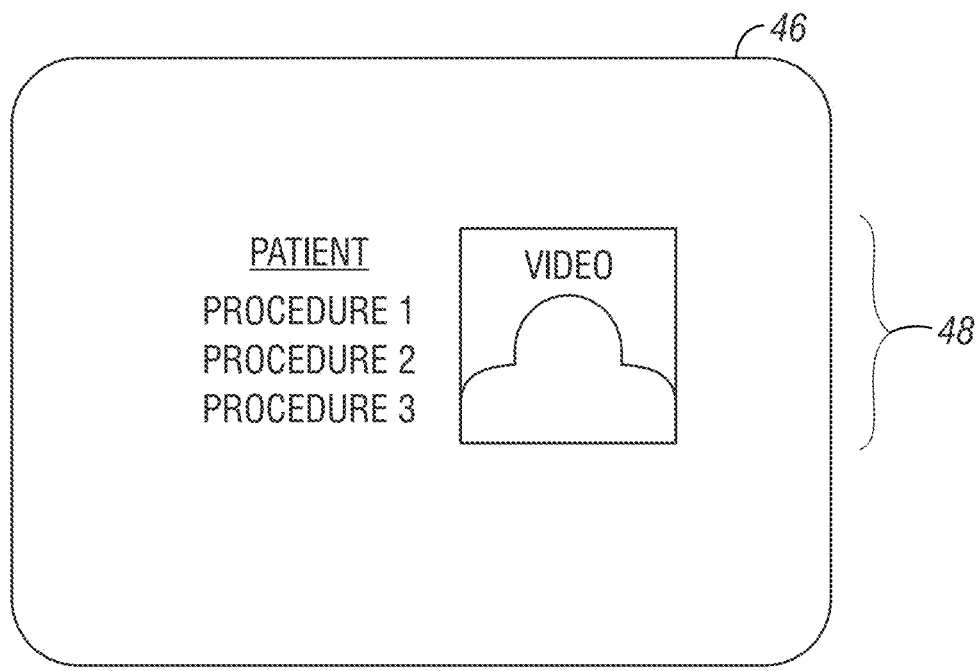
FIG. 4 is a screen display of a user interface for a patient to review informed consent videos.

FIG. 4 illustrates one example of a portal 46 where a patient may view examples of informed consent 48 which they have previously given. Thus, after a visit with a health care provider, a patient can go back and review informed consent videos if they would like. Alternatively, the informed consent video may be stored on a computer readable storage media such as USB drives and given to the patient at the time of the visit.

Figure 5:
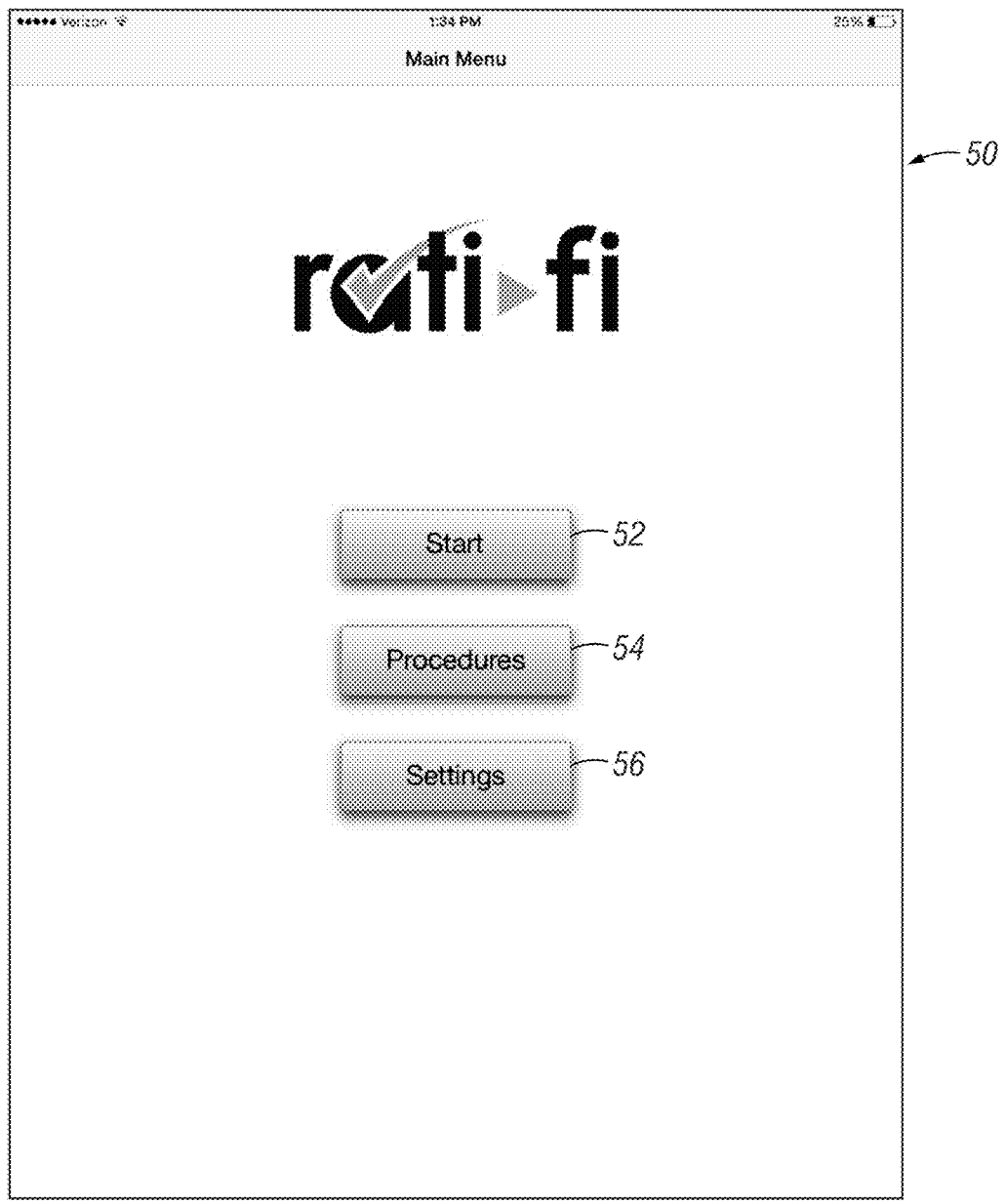
FIG. 5 is a screen display from a mobile app for obtaining informed consent.

FIG. 5 is a screen display 50 from a mobile app for obtaining informed consent. As shown on a "Main Menu", there is a "Start" button 52, a "Procedures" button 54, and a "Settings" button 56. The mobile app may be operated by a health care provider in order to obtain informed consent from patients.

Figure 6:
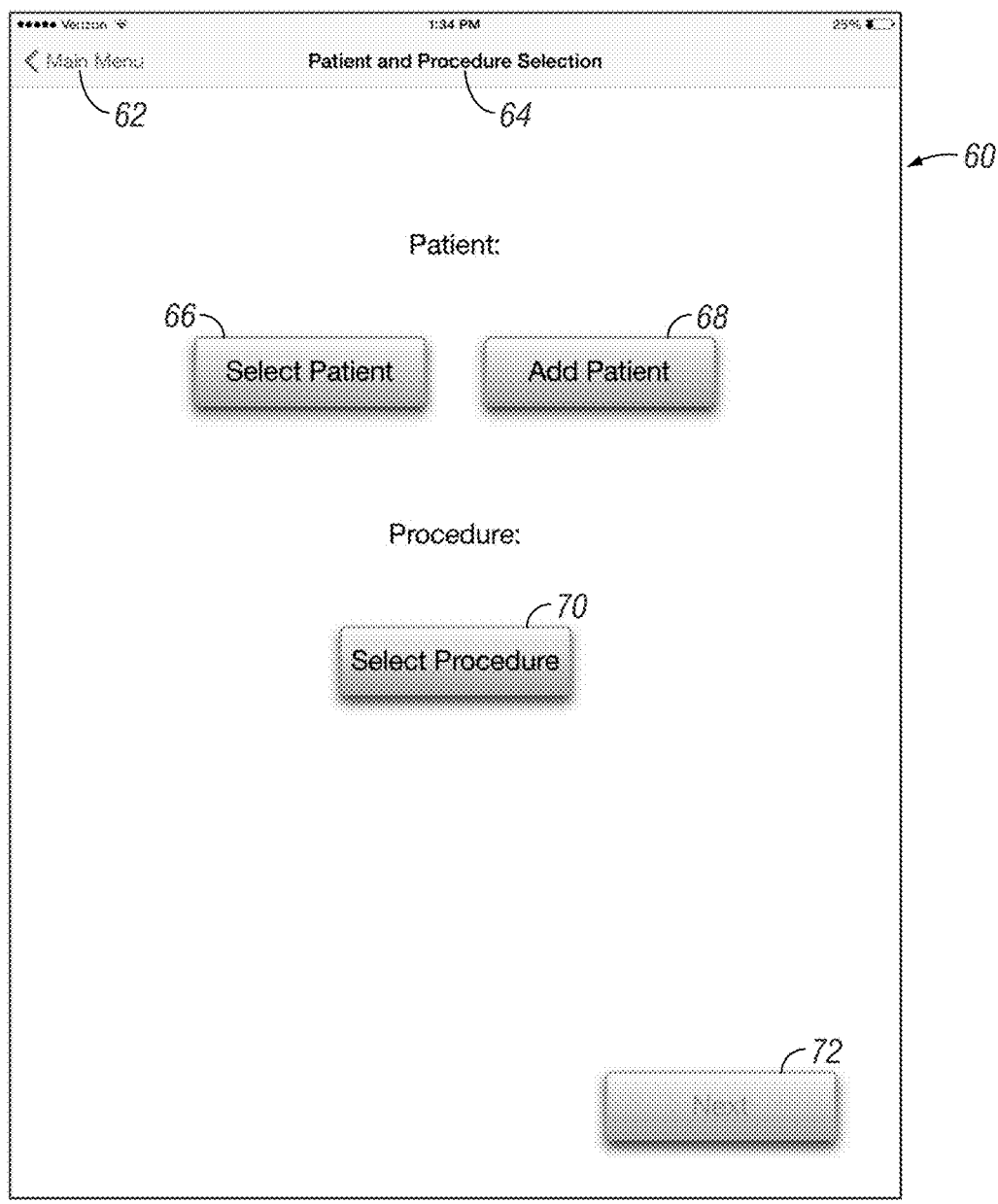
FIG. 6 is a screen display for a mobile app allowing a user to select a patient, add a patient, or select a procedure.

FIG. 6 is a screen display 60 for a mobile app allowing a user to select a patient using a "Select Patient" button 66, add a patient using an "Add Patient" button, or select a procedure using a "Select Procedure" button. The screen is identified as a "Patient and Procedure Selection" screen 64. A user can navigate back to the "Main Menu" 62. Once appropriate patient and procedure selections have been made a user can advance by selecting the "Next" button 72. The "Next" button 72 may be disabled unless and until the patient and procedure selections have been made.

Figure 7:
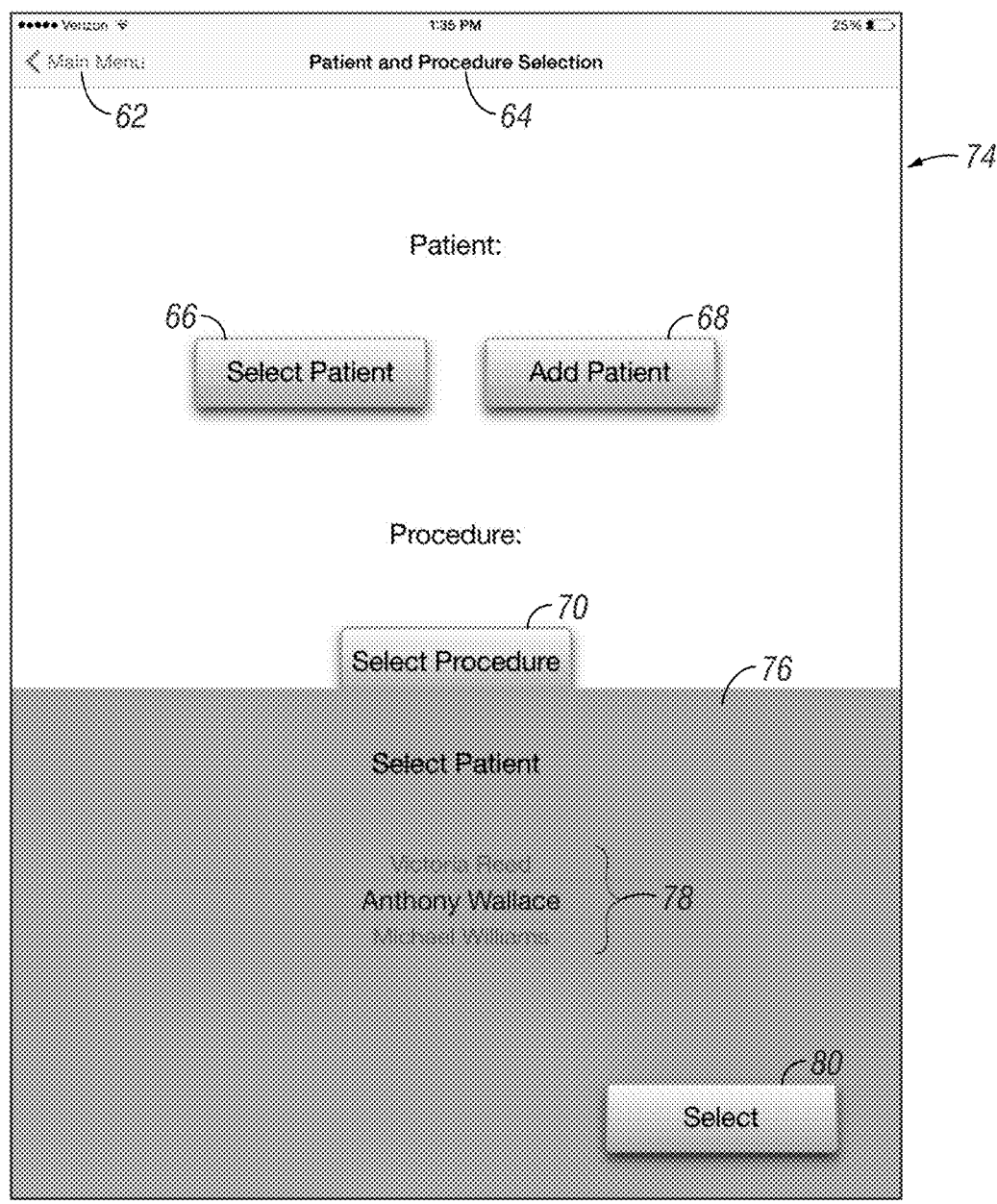
FIG. 7 is a screen display for a mobile app for obtaining informed consent where a user is permitted to select a patient.

FIG. 7 is a screen display 74 for a mobile app for obtaining informed consent where a user is permitted to select a patient. A "Select Patient" window 76 is shown which allows a user to select a patient from a list of patients 78 and confirm this selection by using the "Select" button 80.

Figure 8:
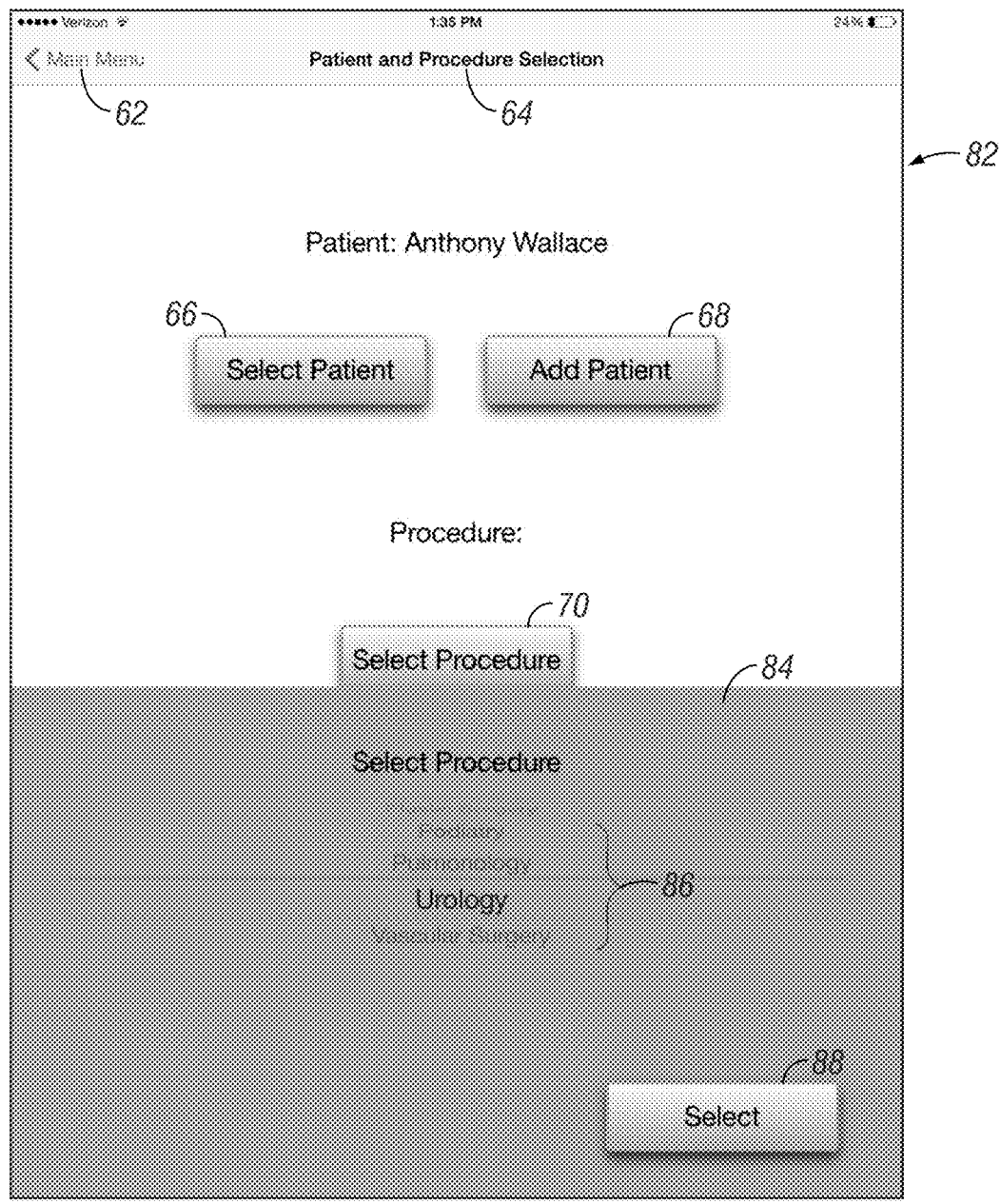
FIG. 8 is a screen display for a mobile app for obtaining informed consent where a user is permitted to select a procedure.

FIG. 8 is a screen display 82 for a mobile app for obtaining informed consent where a user is permitted to select a procedure. Note that the user has already selected a patient. A "Select Procedure" window 84 is shown which allows a user to select a procedure from a list of procedures 86 and confirm this selection by using the "Select" button 88.

Figure 9:
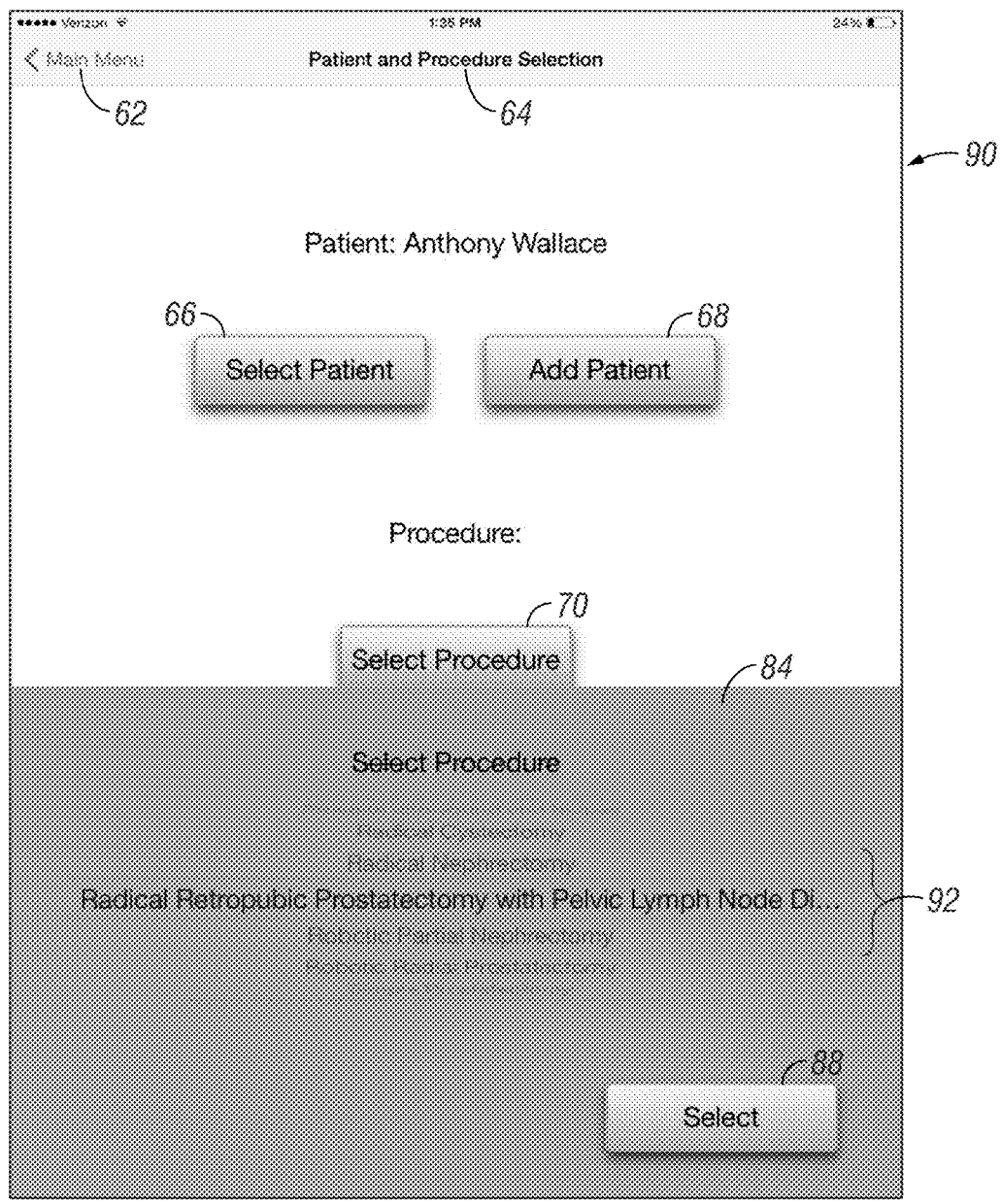
FIG. 9 is another screen display for a mobile app for obtaining informed consent where a user is permitted to select a procedure.

FIG. 9 is another screen display 90 for a mobile app for obtaining informed consent where a user is permitted to select a procedure. FIG. 9 is similar to FIG. 8, however a different procedure within the list of procedures 92 is selected, in this case a Radical Retropubic Prostatectomy with Pelvic Lymph Node Dissection.

Figure 10:
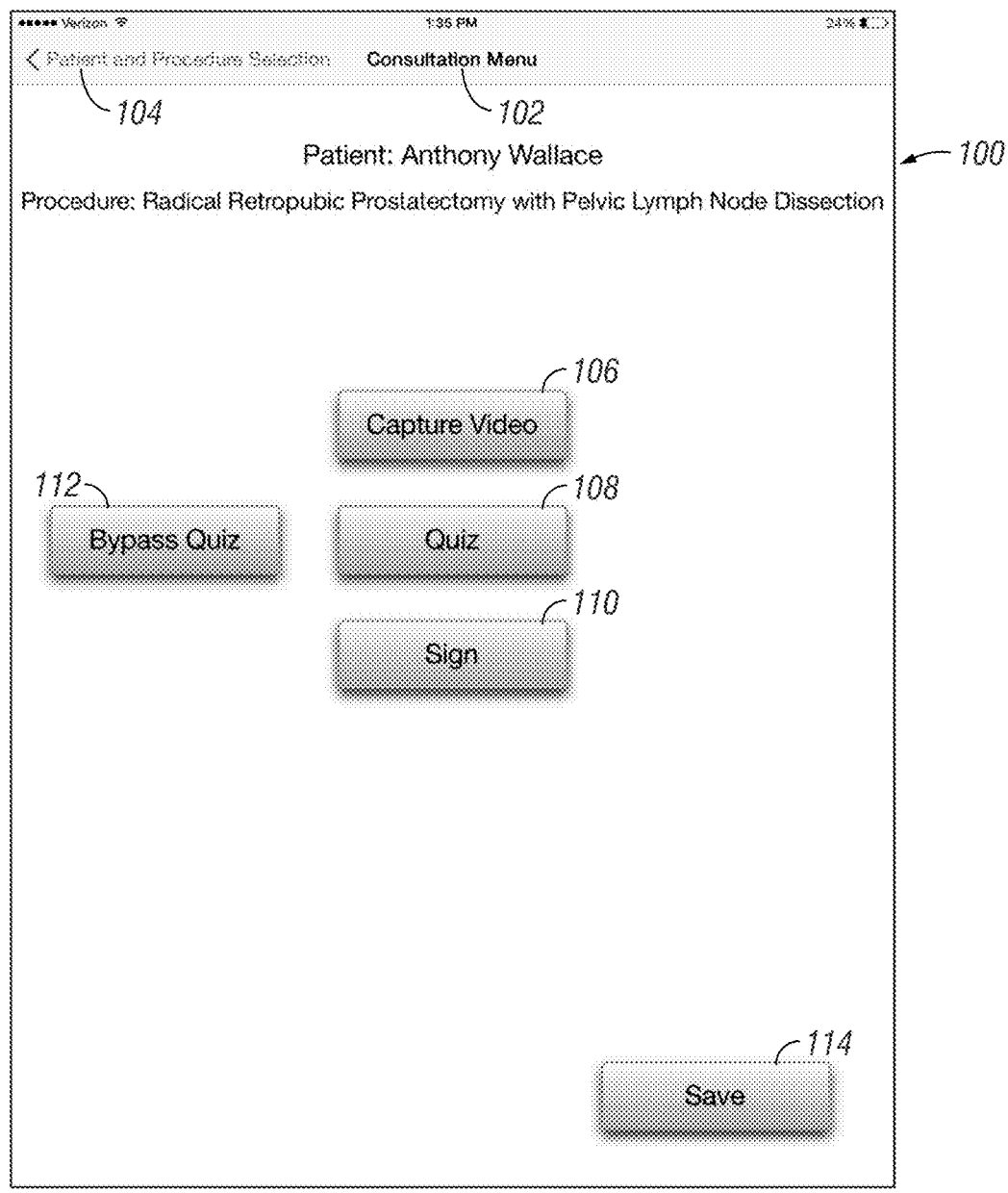
FIG. 10 is a screen display for a mobile app which includes a consultation menu.

FIG. 10 is a screen display 100 for a mobile app which includes a consultation menu 102. The user may select to return to the Procedure Selection 104. As shown in FIG. 10, there are buttons for "Capture Video" 106, "Quiz" 108, "Sign", 110, and "Bypass Quiz" 112. There is also a "Save" button 114.

Figure 11:
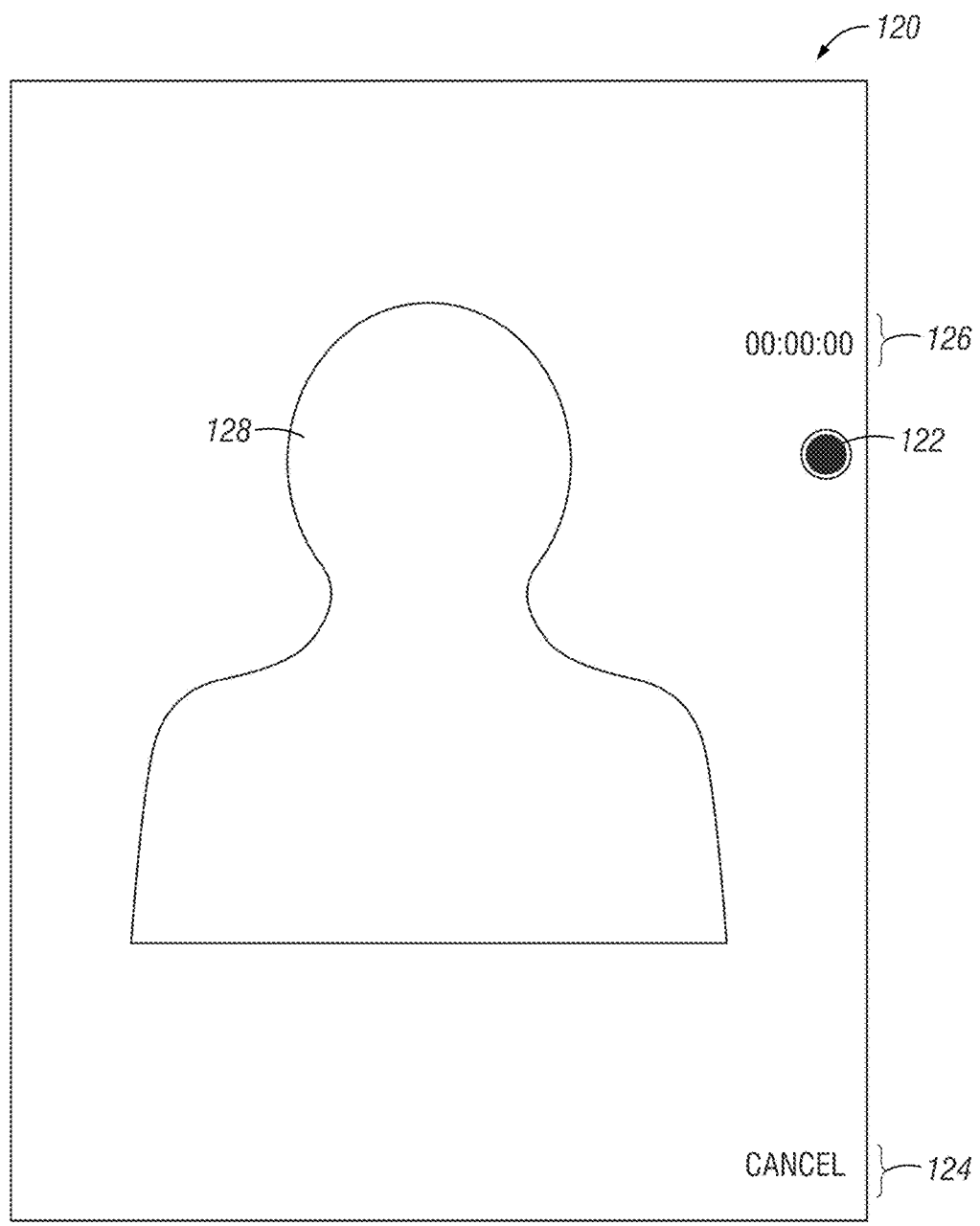
FIG. 11 is screen display for a mobile app which displays video of a patient.

FIG. 11 is screen display 120 for a mobile app which displays video of a health care provider 128. A timer 126 may be present as well as a record/stop button 122 and an option to "Cancel" 124. Thus, video of the health care may be recorded to assist in documenting the informed consent of the patient.

Figure 12:
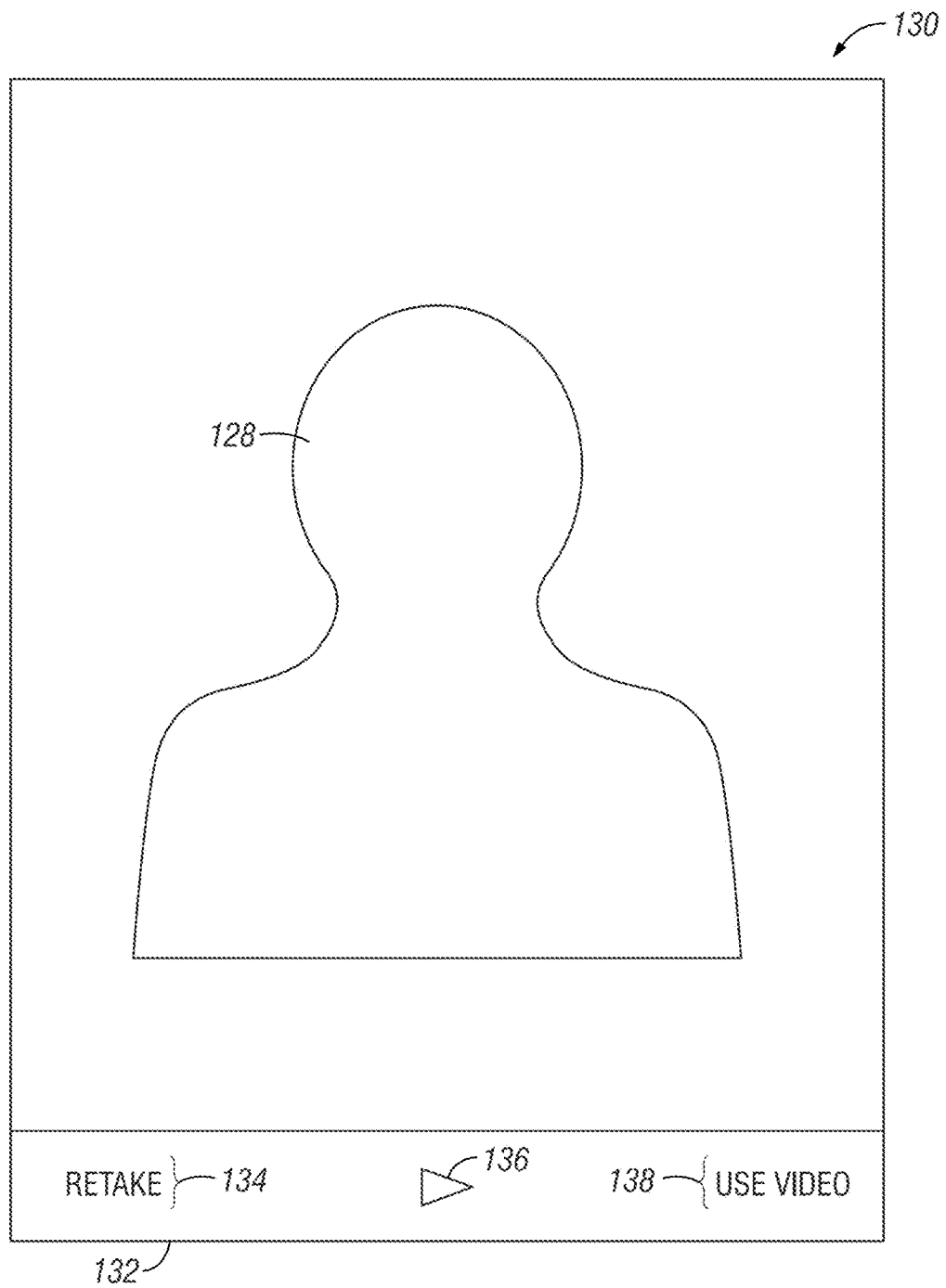
FIG. 12 is another screen display for a mobile app which displays video of a patient.

FIG. 12 is another screen display 130 for a mobile app which displays a video. The screen display 130 may be displayed after video has been recorded. User options are shown along the bottom of the screen display 130. The user may select "Retake" to retake the video if they are unsatisfied for any reason. A "play" button 137 is shown to play the video. If the user is content with the video then they may select to "Use Video" 138.

Figure 13:
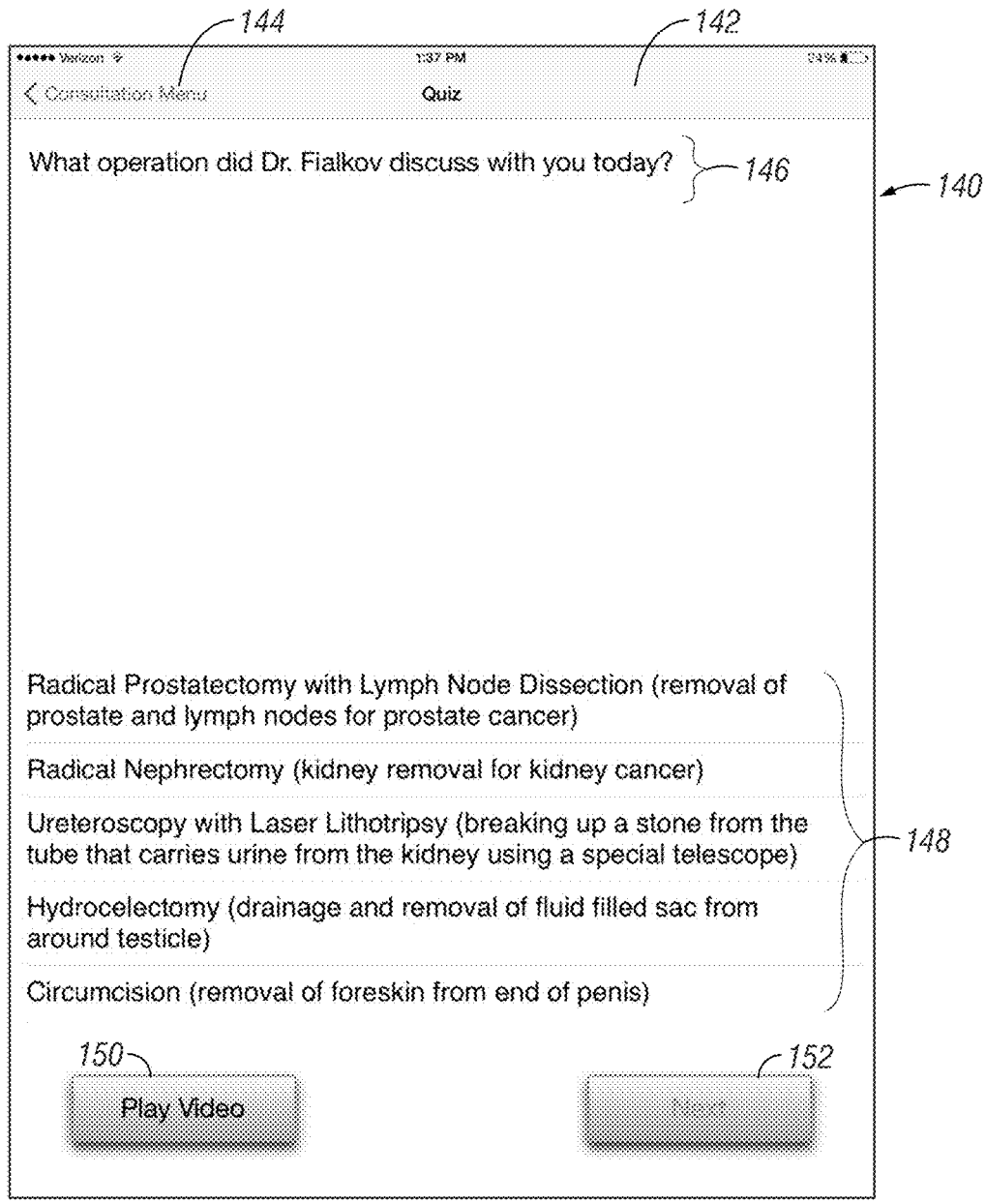
FIG. 13 is a screen display for a mobile app which presents a quiz.

FIG. 13 is a screen display 140 for a mobile app which presents a quiz. A menu bar 142 is provided allows the "Consultation Menu" to be selected to return the user to a previous screen. The quiz includes a question 146. Multiple choice answers 148 are also shown. One example of a representative question is "What operation did Dr. Fialkov discuss with you today?" The answers include various examples of operations one of which was actually discussed. The user is also given the option of selecting a "Play Video" button 150. A "Next" button is also shown. The "Next button" may be disabled unless and until an answer is selected.

Figure 14:
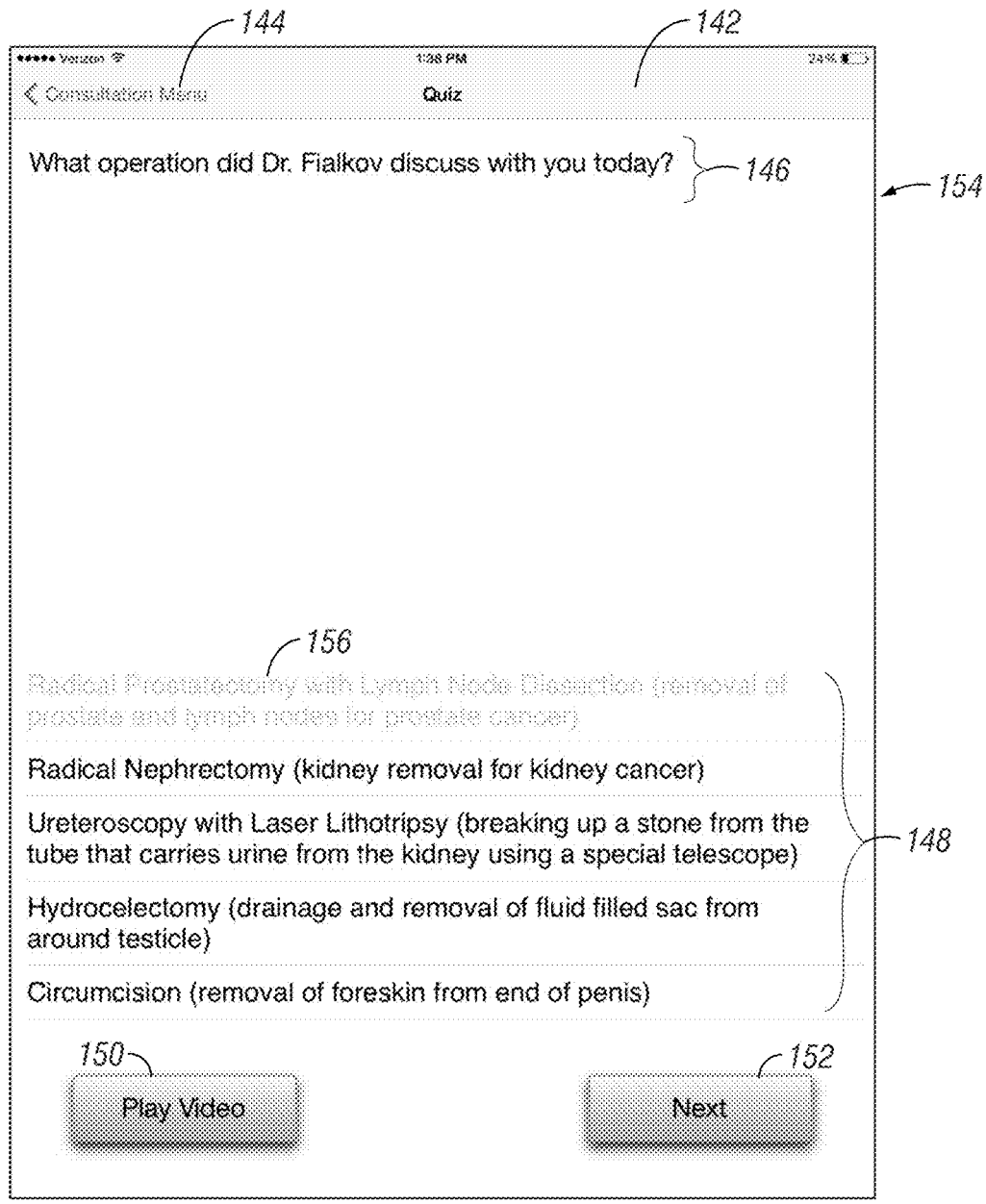
FIG. 14 is a screen display for a mobile app after a patient has selected an answer to a question of a quiz.

FIG. 14 is a screen display 154 for a mobile app after a patient has selected an answer to a question of a quiz, in this instance "Radical Prostatectomy with Lymph Node Dissection (removal of prostate and lymph nodes for prostate cancer" 156. Here, the patient has selected the correct answer to the question.

Figure 15:
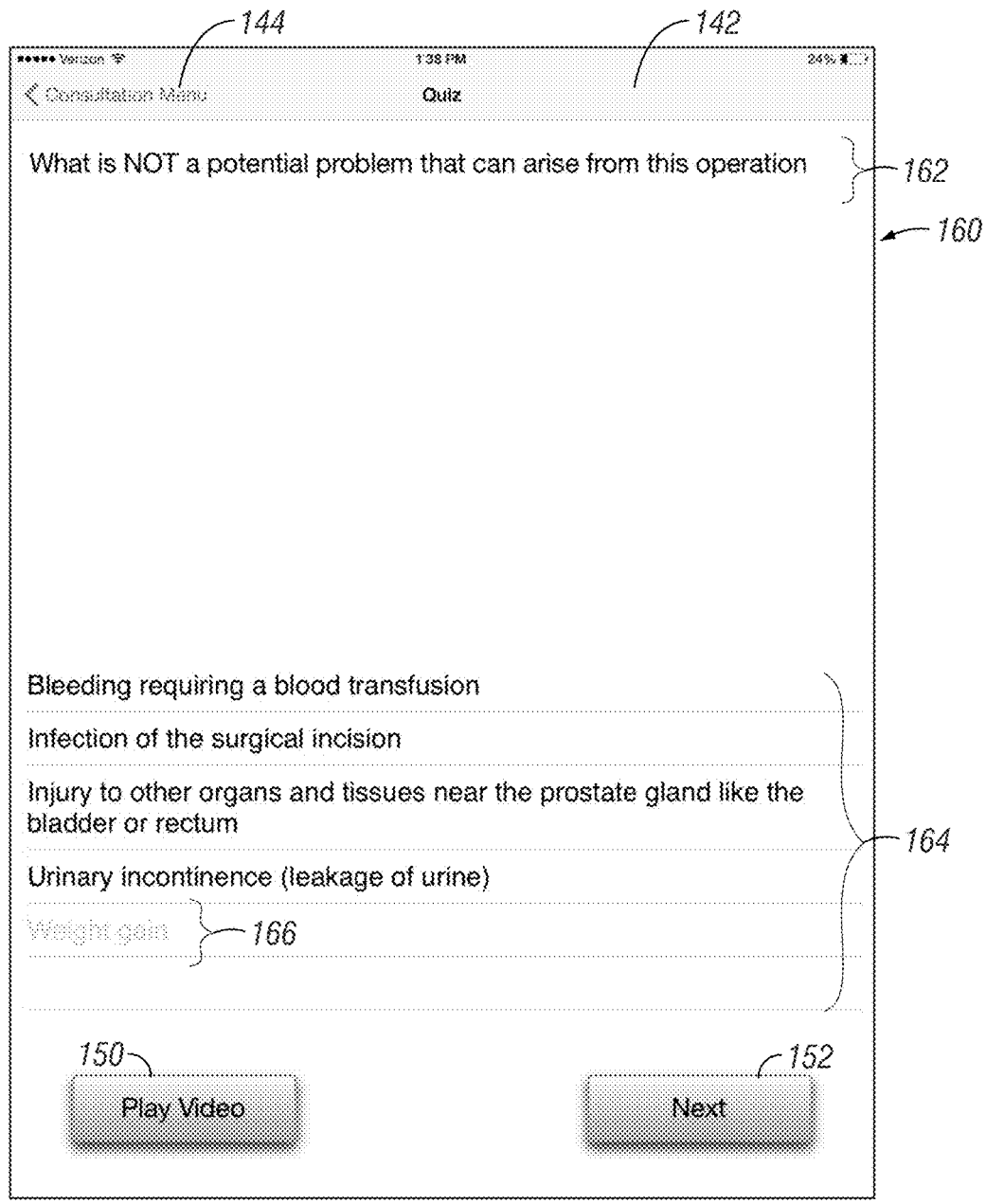
FIG. 15 is a screen display for a mobile app showing another example of a quiz question and an answer has been selected by a patient.

FIG. 15 is a screen display 160 for a mobile app showing another example of a quiz question and an answer has been selected by a patient. Here the question 162 is "What is NOT a potential problem that can arise from this operation?" Various answers 164 are provided. Here a patient has selected "Weight gain" 166 which is also a correct answer.

Figure 16:
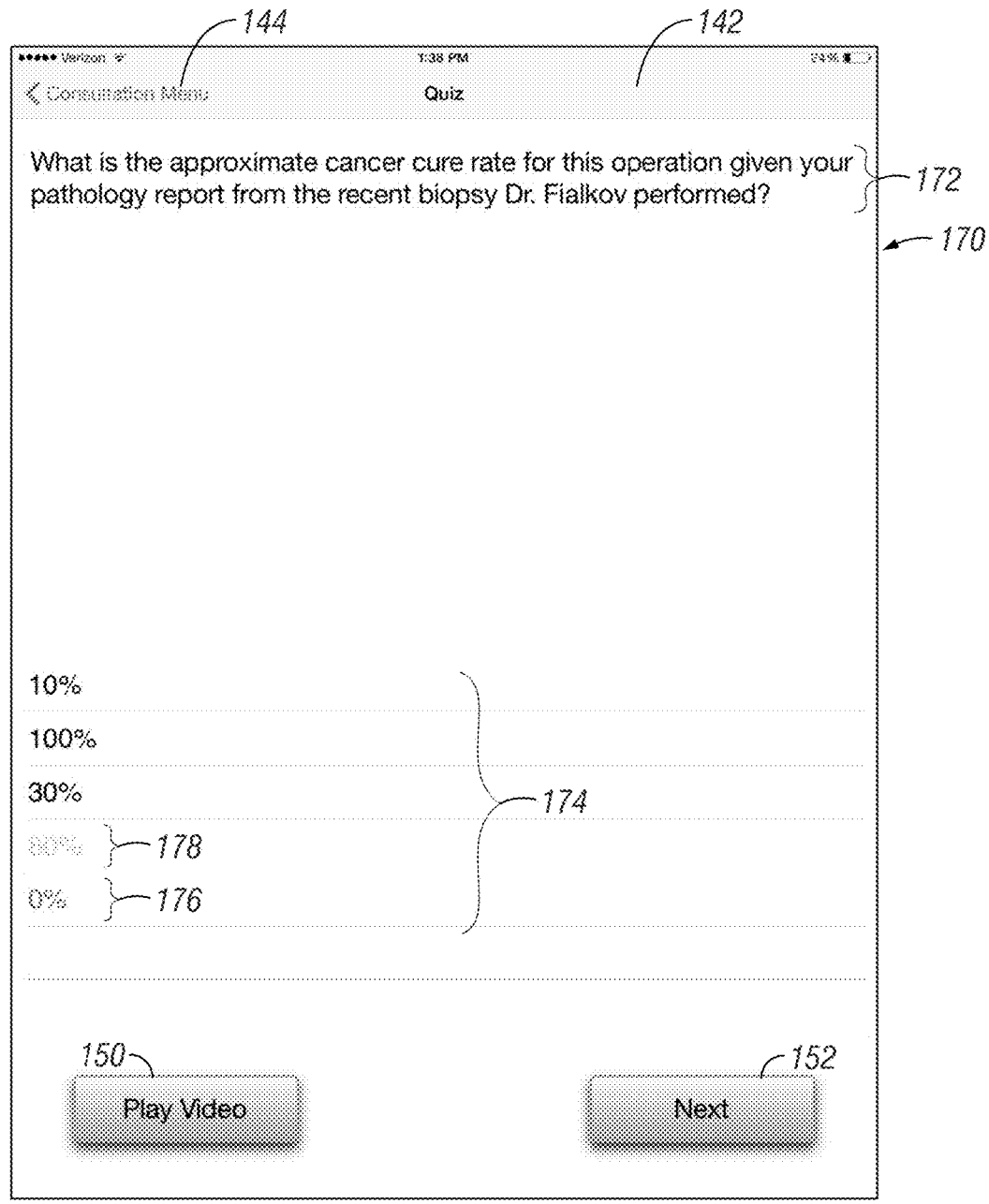
FIG. 16 is a screen display for a mobile app showing yet another example of a quiz question and an answer which has been selected by a patient.

FIG. 16 is a screen display 170 for a mobile app showing yet another example of a quiz question and an answer which has been selected by a patient. Here, the question 172 is "What is the approximate cancer cure rate for this operation given your pathology report from the recent biopsy Dr. Fialkov performed?" Various answers 174 are shown. A patient may select an incorrect answer 176 after which a correct answer 178 may be highlighted or emphasized in a different color. Thus, if the patient responds incorrectly, the patient is immediately informed of the correct answer. If the patient desires they can review the video again by selecting the "Play Video" button 150. Note that the patient may select the "Play Video" button before or after they answer.

Figure 17:
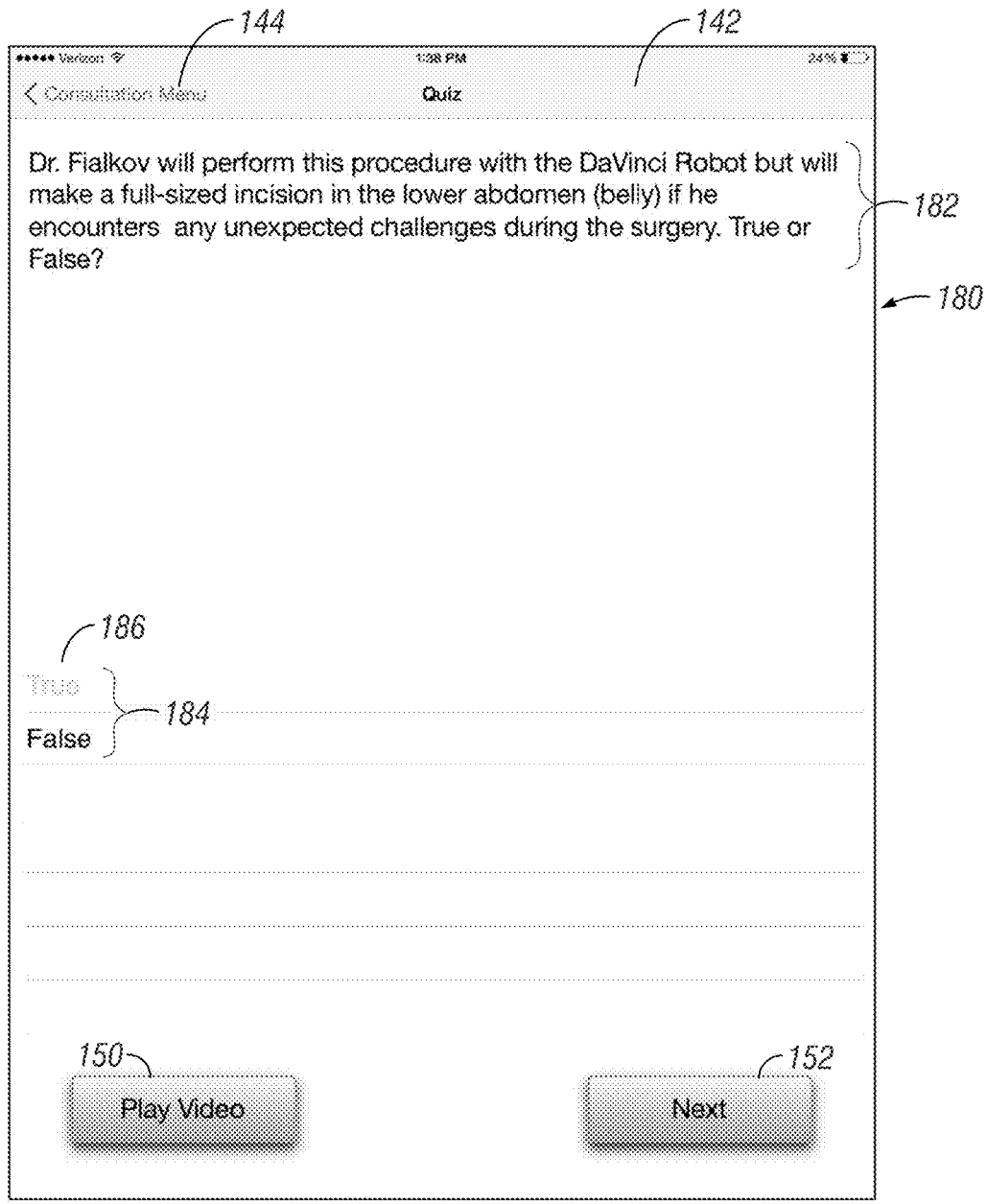
FIG. 17 is a screen display for a mobile app showing an example of a true/false question and answer to a quiz question.

FIG. 17 is a screen display 180 for a mobile app showing an example of a true/false question 182 and answers 184 to the quiz question 182. Here, the correct answer "True" 186 is selected by the patient.

Figure 18:
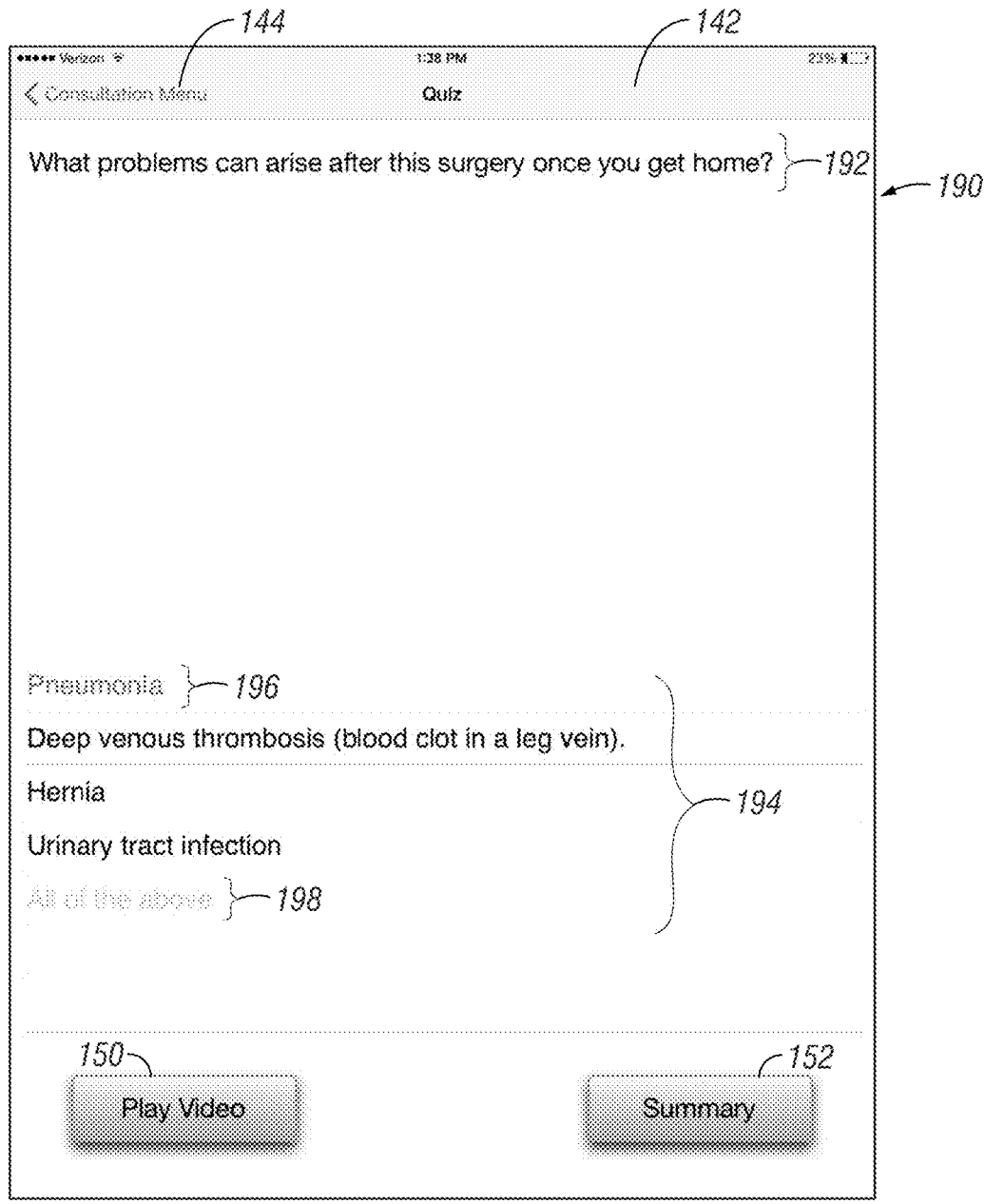
FIG. 18 is a screen display for a mobile app showing an example of a quiz question, a user's answer to the quiz question and a correct answer to the question.

FIG. 18 is a screen display 140 for a mobile app showing an example of a quiz question 192 and multiple choice answers 194. A user's answer 196 to the quiz question 192 is shown as well as the correct or best answer 198. Instead of a next button, a "Summary" button 152 is shown upon completion of the quiz.

Figure 19:
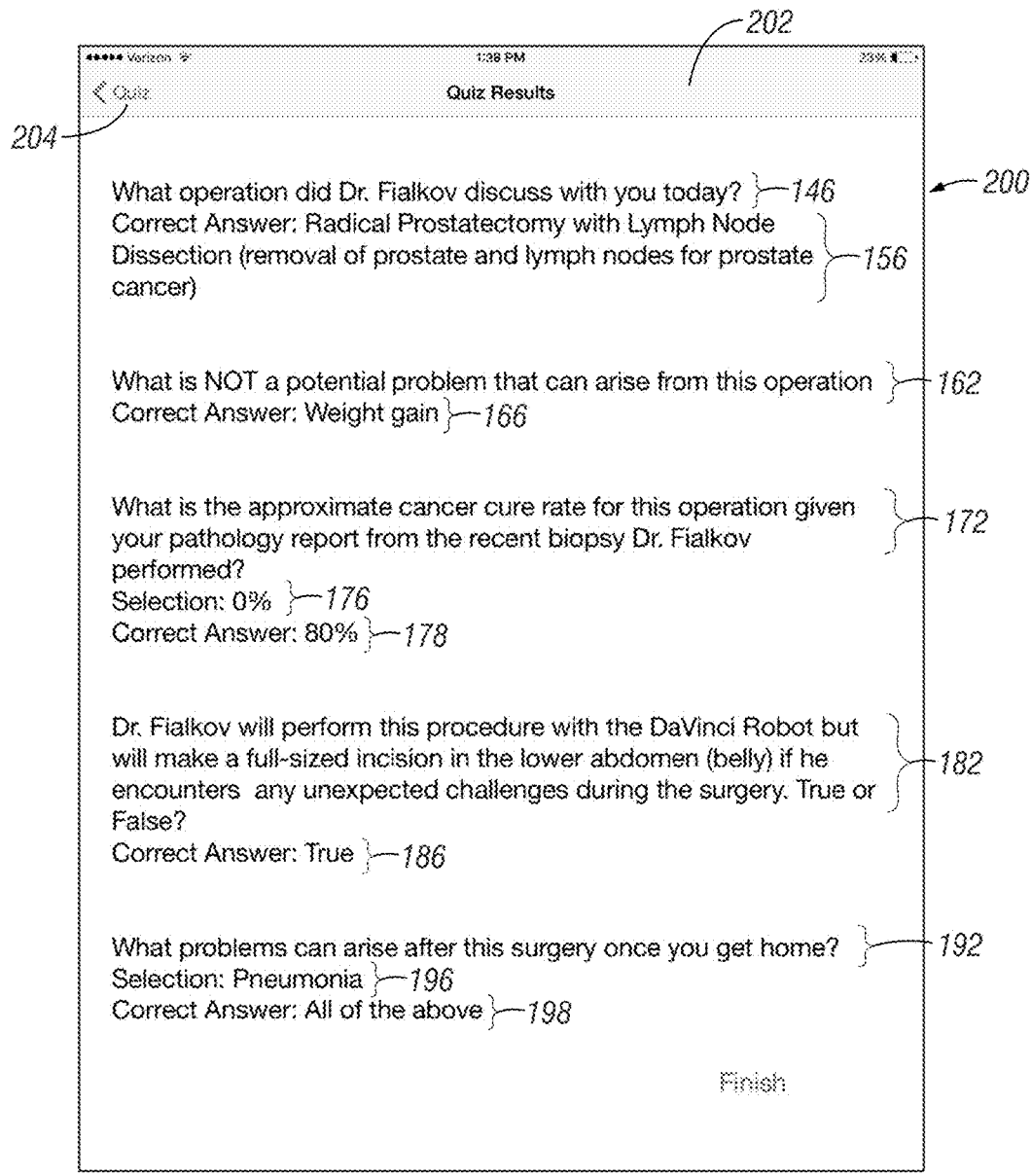
FIG. 19 is a screen display for a mobile app showing an example of quiz results.

FIG. 19 is a screen display 208 for a mobile app showing an example of quiz results 202. A user can return to the quiz by selecting "Quiz" 204. Each of the questions are shown again as well as the correct answer if the correct answer was selected by the patient. Where the patient did not select the correct answer the patient's selection is also shown. Thus, the patient is able to review all of the quiz questions and answers.

Figure 20:
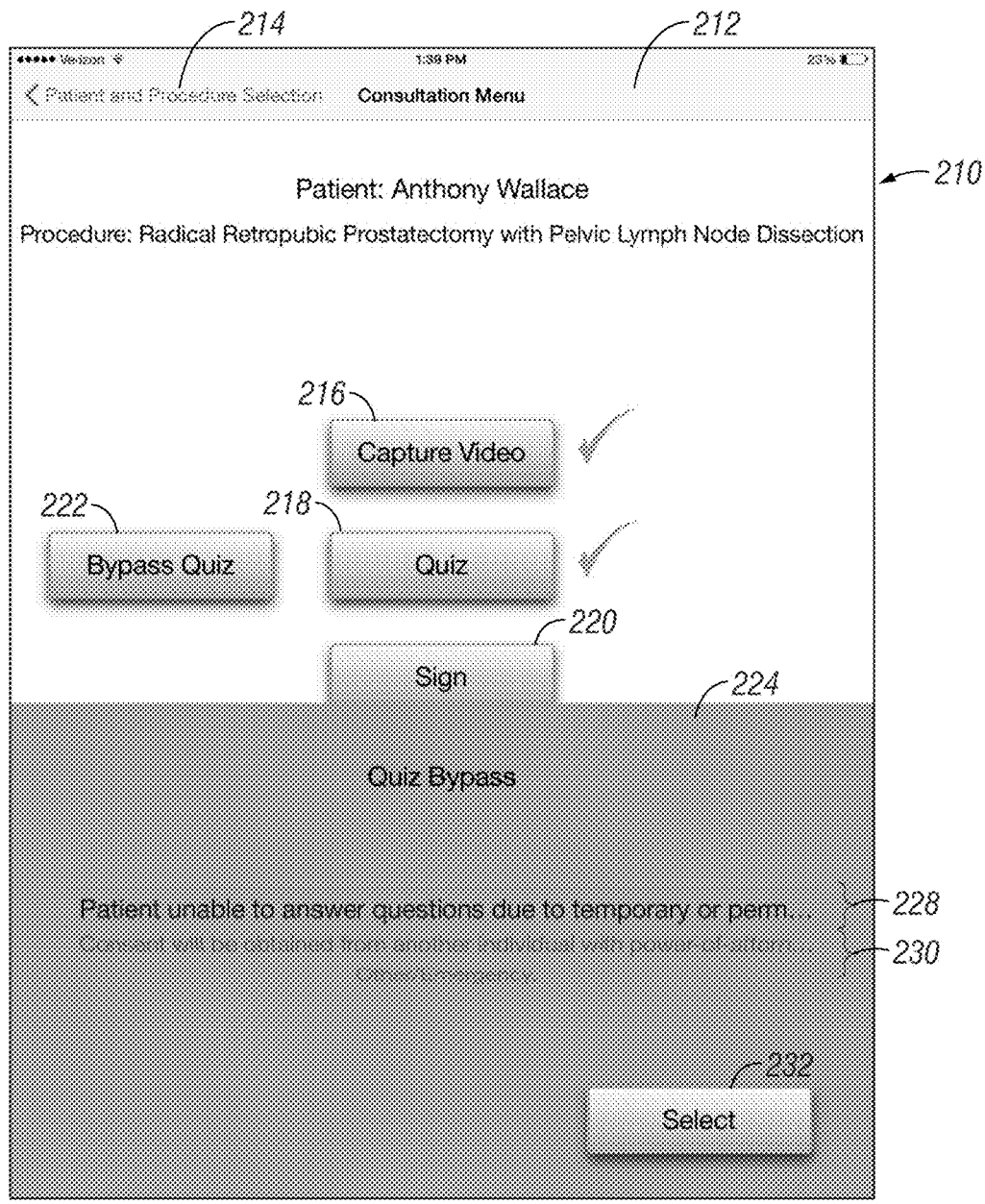
FIG. 20 is a screen display showing a mobile app with a consultation app where a user has selected to the bypass the quiz.

FIG. 20 is a screen display 210 showing a mobile app with a consultation app where a user has selected to the bypass the quiz. A quiz bypass area 224 shown which allows a user to select a reason why the quiz is being bypassed. There may be various reasons why it may not be necessary or appropriate to implement the quiz such as the patient being unable to answer questions due to a temporary or permanent incapacity 228 or because consent will be obtained from another individual with power of attorney 230, it is an emergency situation, or other reason. Once the reason to bypass the quiz has been given the user may choose the "Select" button 232.

FIG. 21 is a screen display 240 showing a mobile app with a consent for surgery or procedure document 242. At the top of the screen display a user may select the Consultation Menu 246 to return to the previous screen or choose "Save" 244 to save the document after it is has been signed.

Figure 22:
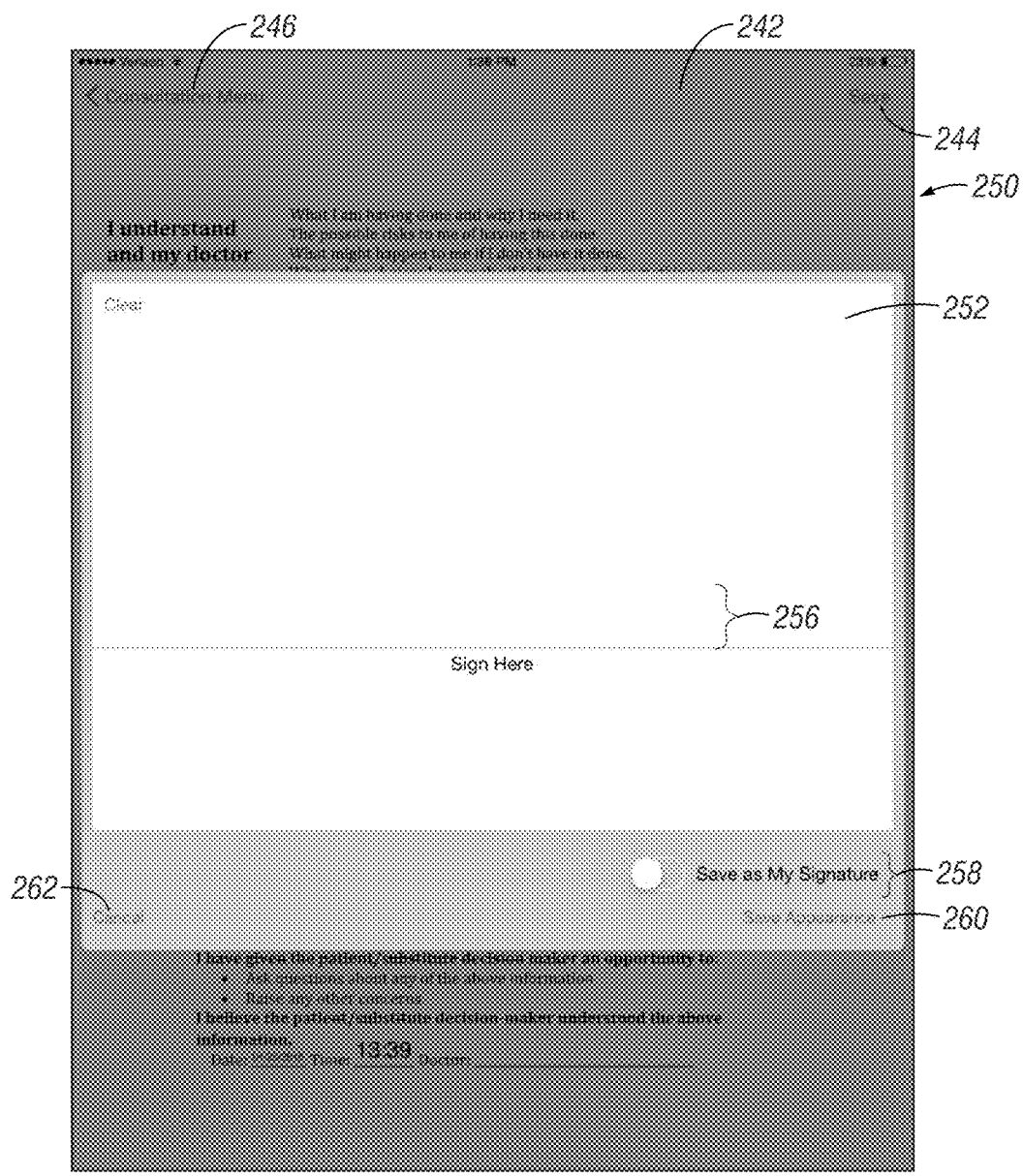
FIG. 22 is a screen display showing a mobile app which allows a patient to sign a consent document.

FIG. 22 is a screen display 250 showing a mobile app which allows a patient to sign a consent document. A signature area 252 is shown allowing a patient or other authorized individual to sign above the signature line 256. An option for saving the signature 258 is presented as well as an option to "Save Appearance". An option to "Cancel" 262 is also provided. Thus after a patient has been informed about a procedure they can sign to indicate their consent.

Figure 23:
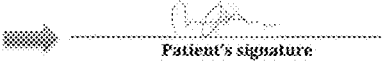
FIG. 23 is a screen display showing a mobile app with a signed consent document.

FIG. 23 illustrates the screen display 250 of FIG. 22 showing a mobile app with a signed consent document after a patient has provided their signature 256.

Figure 24:
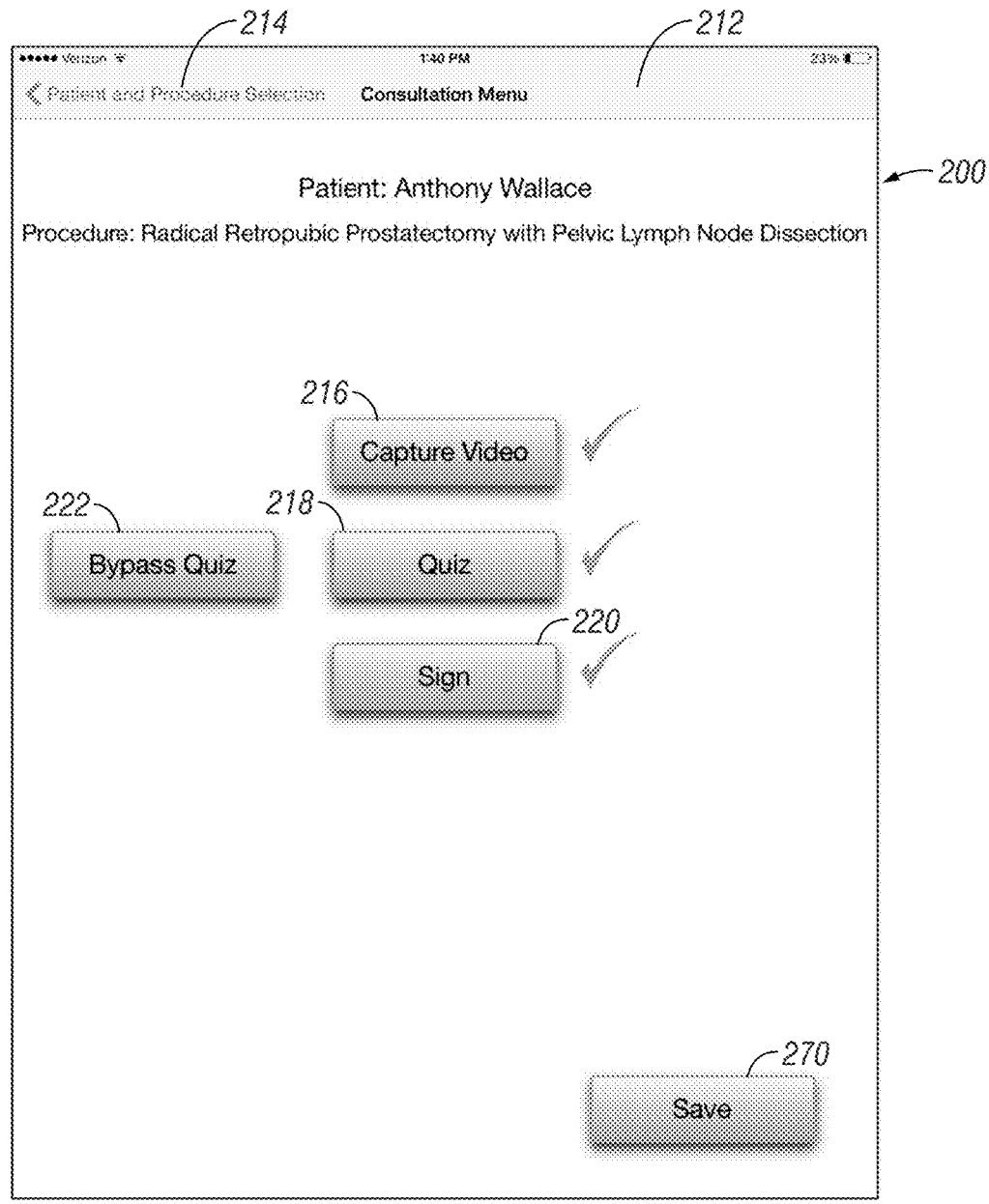
FIG. 24 is a screen display for a mobile app showing a patient, a procedure, and indicating that video has been captured, a quiz has been completed, and a signature has been provided.

FIG. 24 illustrates the screen display 200 for a mobile app showing a patient showing the consultation menu 212. As shown in FIG. 24, there are checkmarks to indicate that different steps have been performed. In particular, it is clear that video has been captured, the quiz has been completed, and a signature has been provided. The "Save" button 270 can be selected to save the information associated with the procedure.

Figure 25:
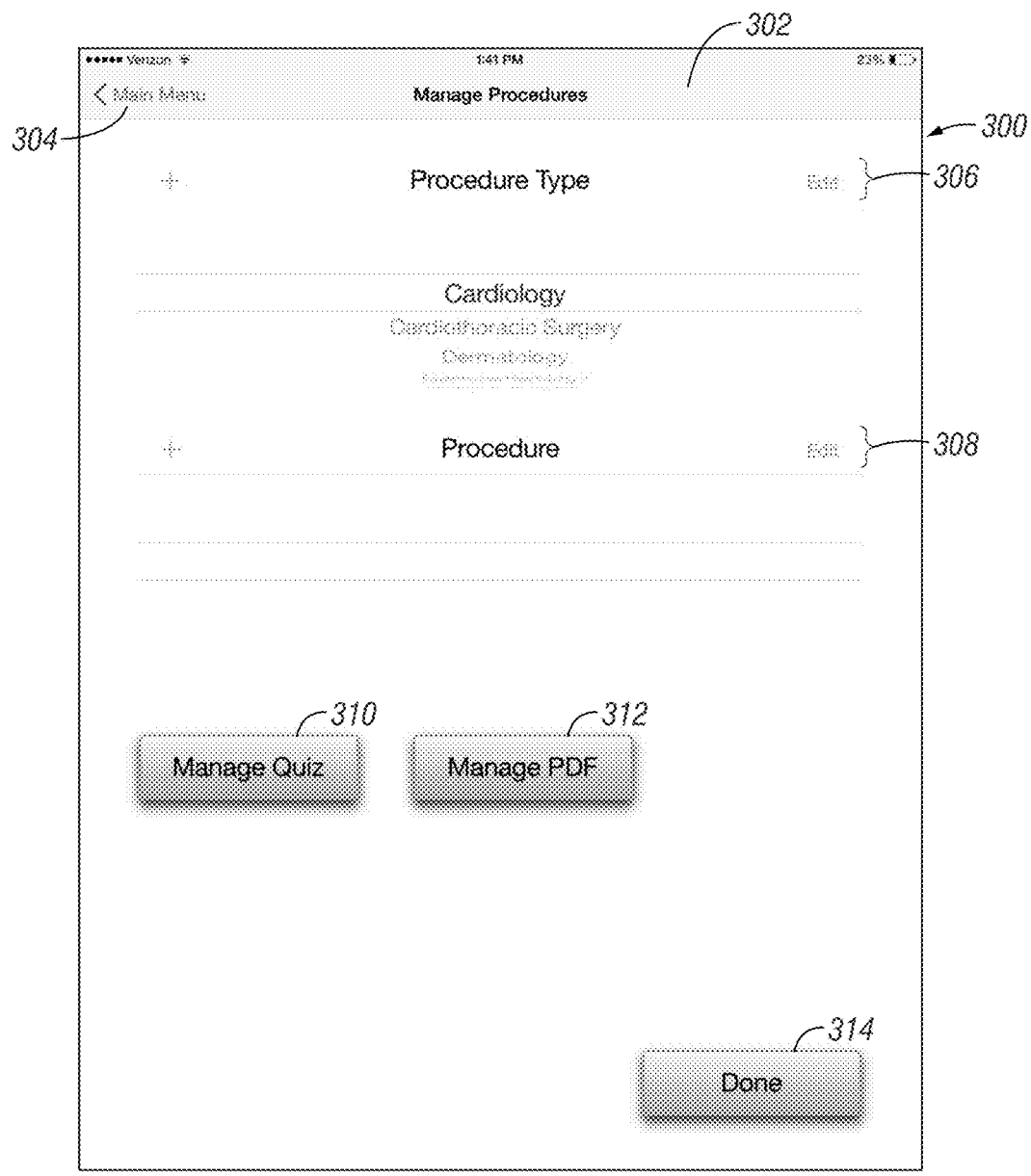
FIG. 25 is a screen display for a mobile app showing a manage procedure screen.

FIG. 25 is a screen display 300 for a mobile app showing a manage procedure screen. This allows a health care provider using the mobile app to setup different types of procedures by selecting to "Edit" 306 procedure types and "Edit" 308 different procedure types. There is a "Manage Quiz" button 310 and a "Manage PDF" button 312. A "Done" button 314 is also shown.

Figure 26:
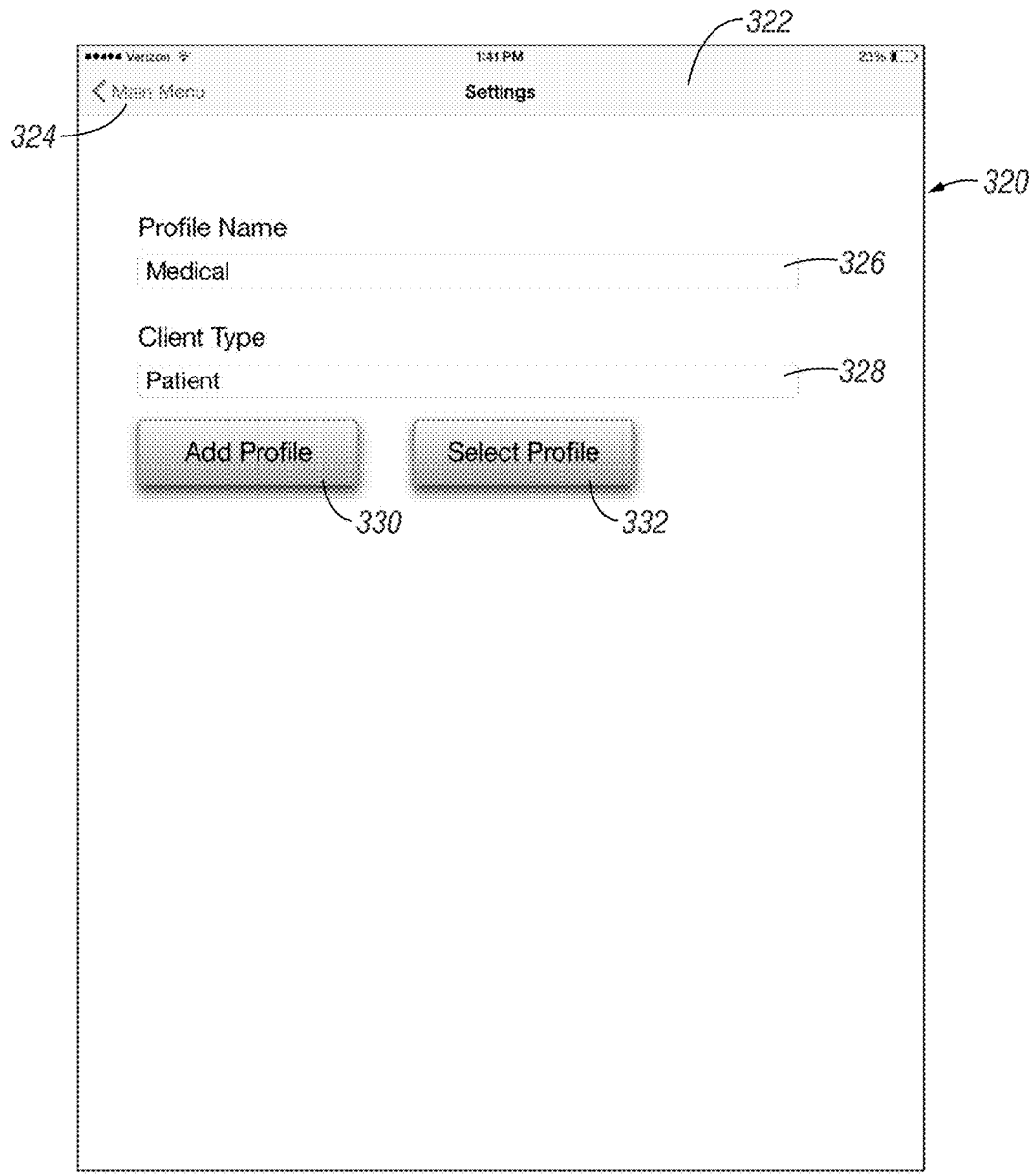
FIG. 26 is a screen display for a mobile app showing a settings screen.

FIG. 26 is a screen display 320 for a mobile app showing a settings 322 screen. A user may select "Main Menu" 324 to return to the main menu if the user chooses to do so. The user is allowed to enter a profile name 326 and a client type 328. The user can select to "Add Profile" 330 or "Select Profile" 332.

Figure 27:
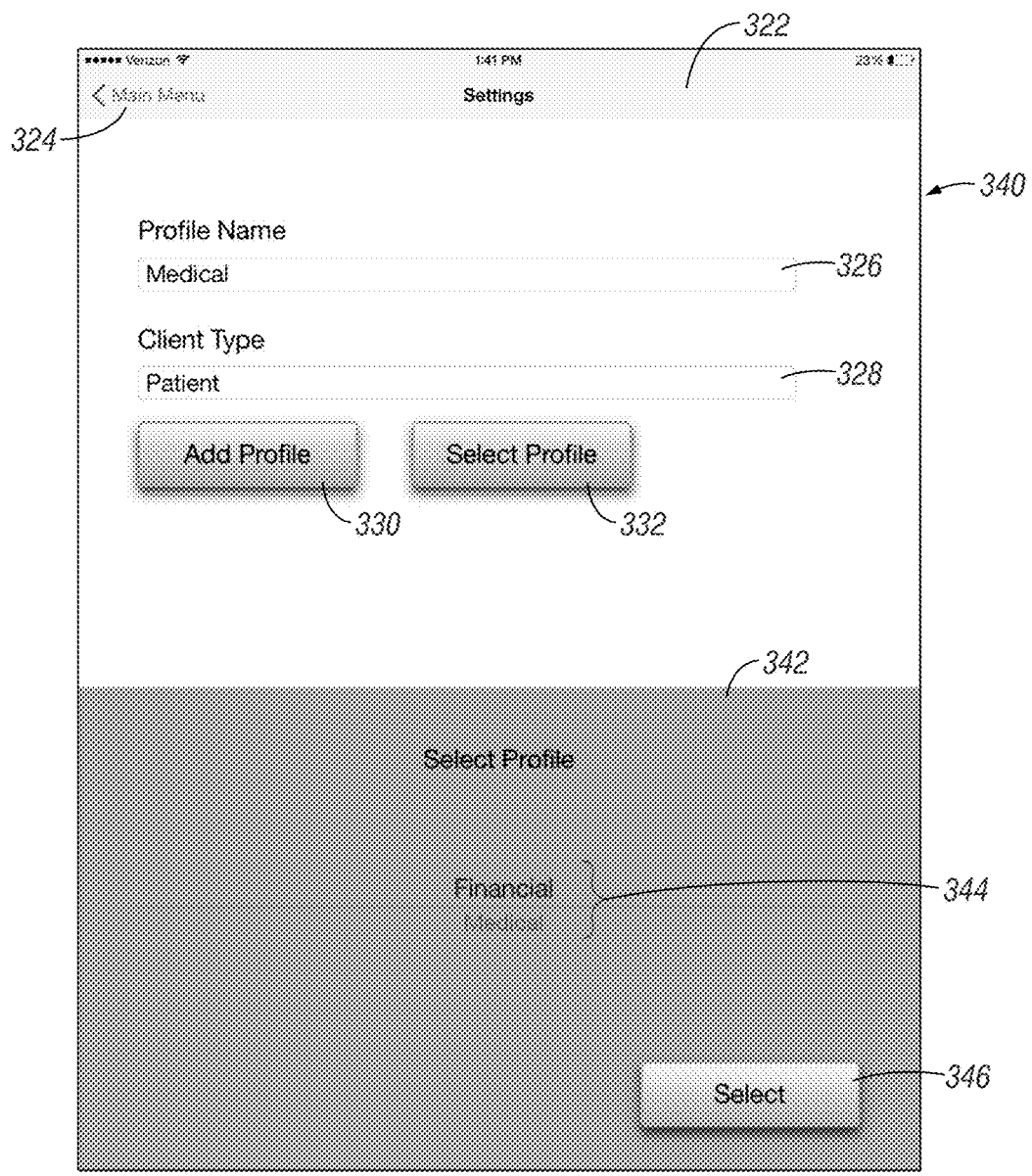
FIG. 27 is a screen display for a mobile app showing a settings screen where a profile is selected.

FIG. 27 is a screen display 340 for a mobile app showing a settings screen where a profile is selected. Here an area 342 is shown with a set of profiles 344 from which the user can select. Thus, the app can be configured for different uses such as financial, medical, legal, etc. There are numerous examples of situations where informed consent is important and/or where one party has a duty or obligation to obtain informed consent from another party.

Figure 28:
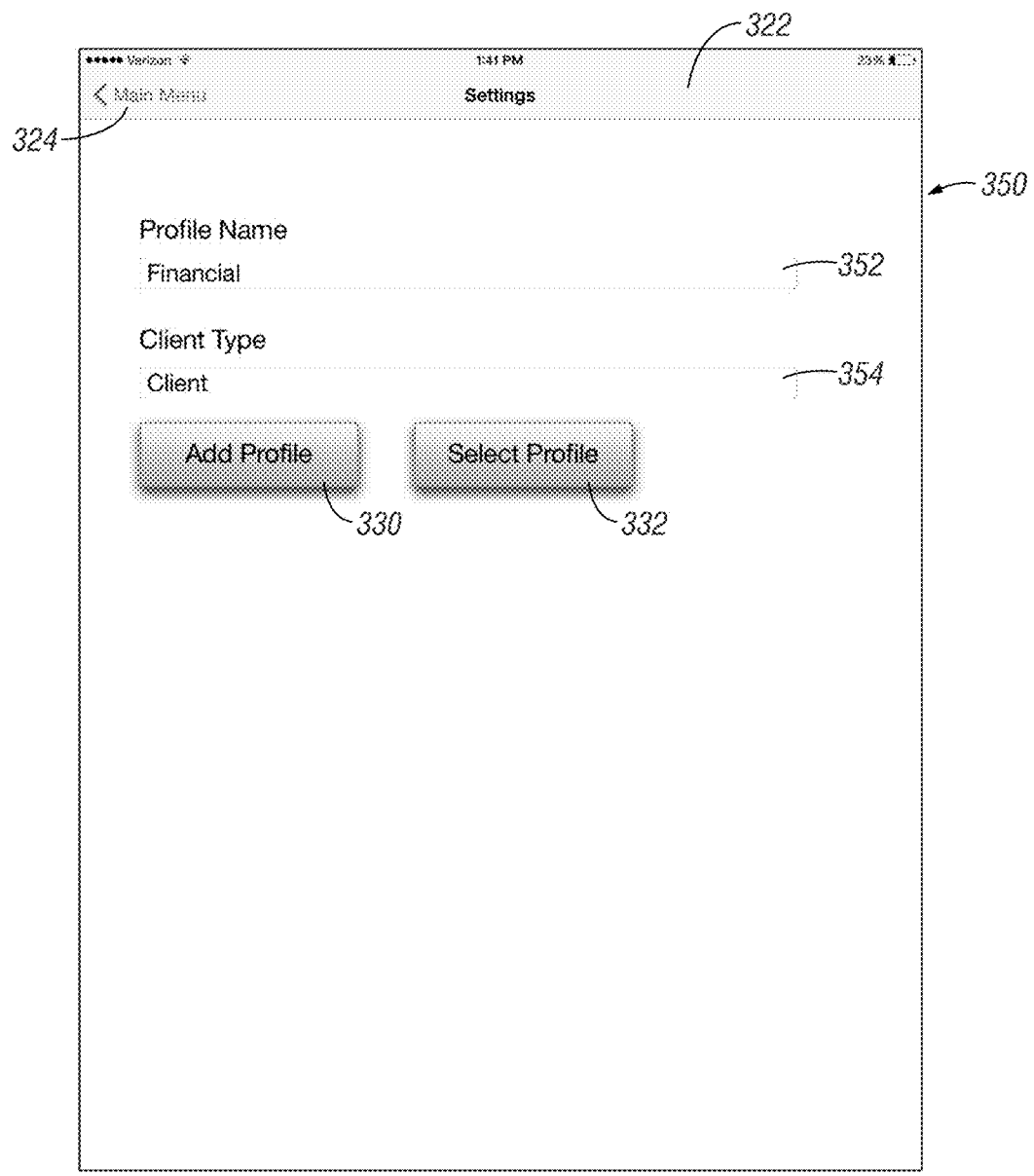
FIG. 28 is another example of a screen display for a mobile app showing a settings screen.

FIG. 28 is another example of a screen display 350 for a mobile app showing a settings screen. Note that in FIG. 28 the profile name shown is "Financial" 352.

Figure 29:
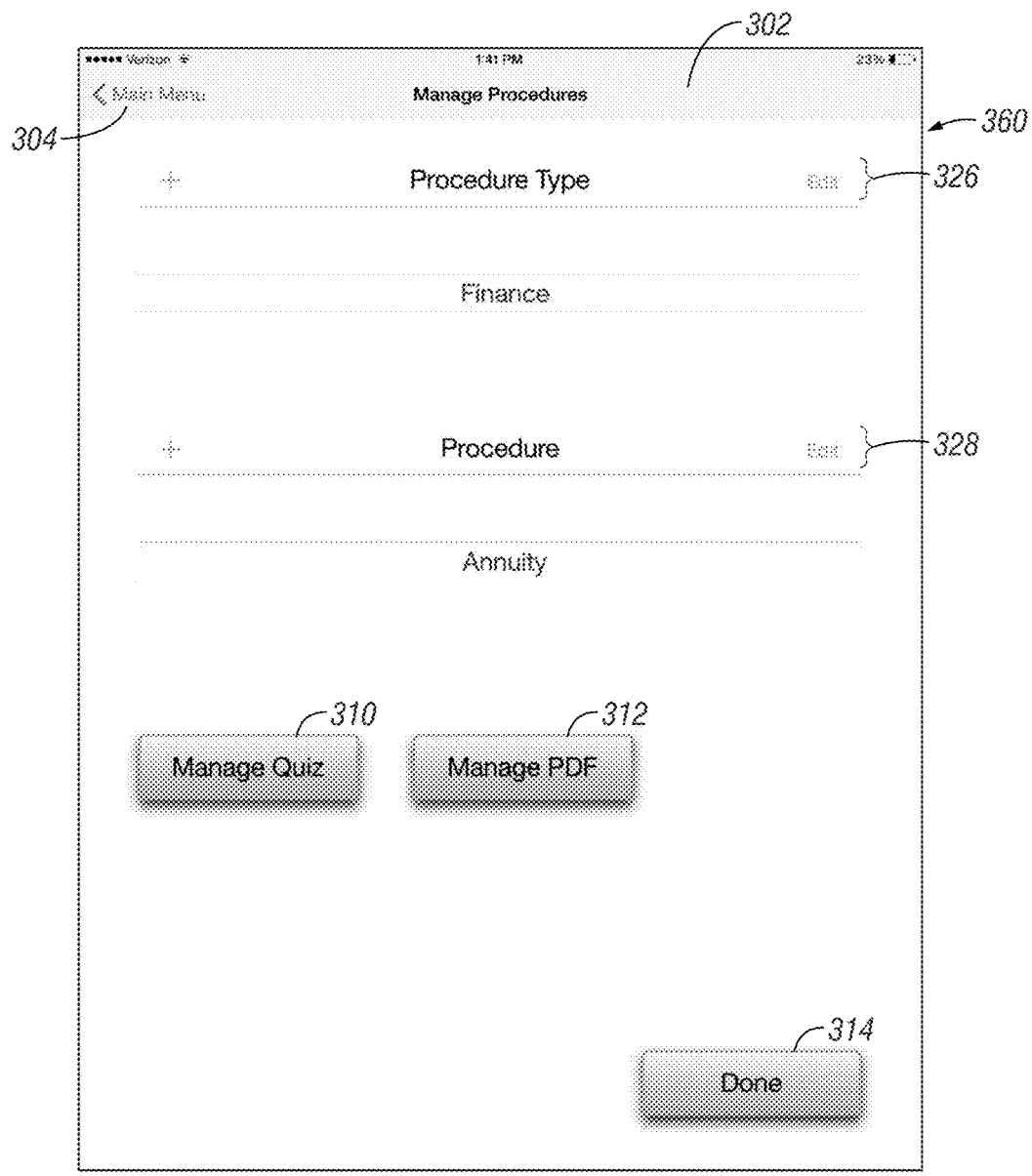
FIG. 29 is a screen display to manage procedures.

FIG. 29 is a screen display 360 for managing procedures. Here the type of procedure is "Finance" and the procedure is "Annuity." Thus, there are many possible uses for the informed consent applications which may be used in financial, legal, medical, or other situations.

It should be understood that a number of features may be incorporated into the mobile app to ensure privacy and security. For example, it is contemplated that a patient using a computing device with the app to take the quiz, for example, would not be able to see the screen which would allow them to see the names of other patients. This can be accomplished by requiring the health care provider's password to view such a screen or otherwise locking the patient out from those portions of the app which they are not permitted to view.

It should also be understood that video is preferably not stored on the computing device at all of if so, only temporarily. Instead, video is streamed to a server for storage or alternatively video may be temporarily saved on the computing device for purposes of uploading to the server and then deleted or wiped from the computing device so that no version of the video remains on the computing device. Other patient data may be similarly treated so that patient information including consent documents and quiz results.

Although discussed primarily with respect to informed consent, it is noted that the use of the video cameras in the examination rooms can be used for other purposes related to documenting patient encounters. For example, health care providers are often subjected to false accusations. Accusations of any sort are taken very seriously and investigated thoroughly which can be time consuming for investigators as well as the health care provider involved. Moreover, even unsubstantiated allegations and the mere fact that an investigation took place can have negative effect on the careers of health care providers. Such accusations can include accusations of sexual assault. One way such accusations can be guarded against is to have a female nurse or other staff member present during a male physician's examination of a female patient. However, this unnecessarily uses resources. Having a video camera present makes a record of the encounter which could be used not only to address false accusations of assault or other wrongdoing but to conclusively prove it unfounded and to use as evidence against the false accuser in criminal or civil litigation. Mere knowledge of the use of the video cameras may provide a significant deterrent to false accusations.

This documentation could be used for other purposes including addressing insurance disputes regarding whether procedures occurred and/or the level of care provided (e.g. the diagnosis codes used to support a particular intervention). Thus, it is to be understood that the video system described may be used for purposes other than informed consent.

Although various methods and systems have been described herein, it is to be understood that the present invention is not to be limited to the specific embodiments described. Moreover, the present invention contemplates numerous variations, additions, modifications, options, and alternatives.

What is claimed:

1. A method for obtaining and documenting informed consent in a patient/healthcare provider setting, the method comprising:
   providing a set of components comprising:
      a gateway device for gaining access to the internee;
      a server network in communication with the internet;
      a data storage device in communication with the server network;
      a healthcare information system in communication with the gateway for retrieving and storing healthcare information about plural patients;
      a mobile computing device for use by a healthcare provider and/or a patient or authorized representative of the patient;
      a video camera;
   providing a software application to the mobile computing device for executing on the mobile computing device;
   receiving a selection of a patient identification into the software application executing on the mobile computing device from a list of patients of the healthcare provider with the healthcare information system or by entry of new patient data by the healthcare provider;
   receiving a selection of a medical procedure for which informed consent of the selected patient is desired into the software application executing on the mobile computing device, the medical procedure selected from a set of a plurality of procedures and one more procedure types from the healthcare information system;

receiving through the software application information about the selected procedure for presentation to the selected patient to educate the patient prior to requesting consent from the selected patient, the information comprising content from a library of videos stored in the server network and available from the healthcare provider or others via the mobile application;

making available a quiz for the selected patient using the software application executing on the mobile computing device, the quiz including a plurality of questions about the medical procedure for assessing informed consent;

documenting administration of the quiz to the selected patient using the software application executing on the mobile computing device;

presenting a document for signature to the selected patient using the software application executing on the mobile computing device, the documenting indicative of informed consent for the medical procedure;

receiving a signature on the document from the selected patient or authorized representative of the patient using the software application executing on the mobile computing device;

capturing video with the video camera evidencing informed consent for the medical procedure using the software application executing on the mobile computing device, wherein the video includes video of the selected patient or the authorized representative of the patient acknowledging that they are providing informed consent, and including a timer to record the time the patient takes in making the informed consent and an electronic time/date stamp of the informed consent associated with the video; and sending to the server network from the mobile computing device the video and the document with the signature, and storing the video in a non-transitory computer readable data storage medium associated with the server network to thereby provide for documenting the informed consent of the selected patient for the medical procedure, further comprising making the video of the informed consent previously given available to the selected patient or an authorized representative of the patient through a portal associated with the server network, the video being sent by streaming or uploading from the mobile computing device after which the video is automatically deleted from the mobile device;

further comprising combining data from the health care information system with the video recording for the selected patient for review by the patient or authorized representative of the patient and the healthcare provider, and documentation of the selected patient's healthcare records.

2. The method of claim 1 wherein the capturing video is performing using a camera integrated into the computing device.

3. The method of claim 1 further comprising receiving a selection of an option to bypass the quiz and documenting a reason for bypassing the quiz by sending the reason to the server.

4. The method of claim 1 further comprising making the video available to a service provider of the individual through a portal associated with the server.

5. The method of claim 1 wherein the video includes video of the individual and a service provider interacting with the individual.

6. The method of claim 1 further comprising receiving through the software application the plurality of questions about the procedure.

* * * * *

UNITED STATES PATENT AND TRADEMARK OFFICE
CERTIFICATE OF CORRECTION

PATENT NO.         : 10,366,463 B2
APPLICATION NO.    : 14/622978
DATED              : July 30, 2019
INVENTOR(S)        : Jonathan Fialkov Page 1 of 1

It is certified that error appears in the above-identified patent and that said Letters Patent is hereby corrected as shown below:

In the Claims

In Claim 1 at Column 10, Line 44:
DELETE: "internee;"
INSERT: --internet;--

In Claim 1 at Column 10, Line 66:
INSERT: --or-- after the word one

Signed and Sealed this
Twenty-fourth Day of September, 2019

Andrei Iancu
*Director of the United States Patent and Trademark Office*